United States Patent [19]
Raad et al.

[11] Patent Number: 5,688,516
[45] Date of Patent: Nov. 18, 1997

[54] NON-GLYCOPEPTIDE ANTIMICROBIAL AGENTS IN COMBINATION WITH AN ANTICOAGULANT, AN ANTITHROMBOTIC OR A CHELATING AGENT, AND THEIR USES IN, FOR EXAMPLE, THE PREPARATION OF MEDICAL DEVICES

[75] Inventors: Isaam Raad, Houston, Tex.; Robert Sherertz, Winston-Salem, N.C.

[73] Assignees: Board of Regents, The University of Texas System, Austin; Baylor College of Medicine, Houston, both of Tex.; Wake Forest University, Winston-Salem, N.C.

[21] Appl. No.: 317,309

[22] Filed: Oct. 3, 1994

Related U.S. Application Data

[63] Continuation-in-part of Ser. No. 150,472, Nov. 12, 1993, abandoned, which is a continuation-in-part of Ser. No. 975,486, Nov. 12, 1992, Pat. No. 5,362,754.

[51] Int. Cl.$^6$ .................. A01N 25/08; A01N 37/12; A61F 2/02; A61M 31/00
[52] U.S. Cl. .................. 424/409; 424/405; 424/423; 514/566; 514/836; 604/53
[58] Field of Search .................. 424/405, 409, 424/423; 514/566, 836; 604/53

[56] References Cited

U.S. PATENT DOCUMENTS

| | | | |
|---|---|---|---|
| 4,107,121 | 8/1978 | Stoy | 260/29.6 |
| 4,442,133 | 4/1984 | Greco te al. | 427/3 |
| 4,678,660 | 7/1987 | McGary et al. | 424/25 |
| 4,749,585 | 6/1988 | Greco et al. | 427/2 |
| 4,895,566 | 1/1990 | Lee | 604/266 |
| 4,917,686 | 4/1990 | Bayston et al. | 604/265 |
| 4,952,419 | 8/1990 | De Leon et al. | 427/2 |
| 5,013,306 | 5/1991 | Solomon et al. | 604/265 |
| 5,202,449 | 4/1993 | Hasegawa | 552/206 |
| 5,217,493 | 6/1993 | Raad et al. | 623/11 |
| 5,362,754 | 11/1994 | Raad et al. | 514/566 |

FOREIGN PATENT DOCUMENTS

PCT/US93/10893 2/1994 WIPO.

OTHER PUBLICATIONS

Root et al., "Inhibitory Effect of Disodium EDTA Upon the Growth of Staphylococcus Eipidermis In Vitro: Relation to Infection Prophylaxis of Hickman Catheters" *Antimicrobial Agents and Chemotherapy*, 32(11):1627–1631, 1988, USA.

Adair et al., "Resistance of Pseudomonas to Quaternary Ammonium Compounds," *Applied Microbiology*, 21(6):1058–1063, Jun., 1971.

Beaumont, "In–Vivo Experiments with Ethylenediamine–Tetra–Acetic Acid and Investigations Into Its Action of Penicillin–Resistant *Staphylococcus Aureus*," *The Medical Journal of Australia*, pp. 1017–1020, Nov., 1970.

Brown, "Effects of Microbial Environment of Drug Resistance," *J. Sci. FD Agric.*, 25:227–230, 1974.

Brown and Foster, "Effect of slime on the sensitivity of *Pseudomonas aeruginosa* to EDTA and polymyxin," *Journal of Pharmacy and Pharmacology (Abstract)*, British Pharmaceutical Conference, 108th Meeting, Glasgow, 23(Suppl.):236S, Sep. 13–17, 1971.

(List continued on next page.)

*Primary Examiner*—Carlos Azpuru
*Attorney, Agent, or Firm*—Arnold, White & Durkee

[57] ABSTRACT

Compositions and methods of employing compositions in flushing and coating medical devices are disclosed. The compositions include selected combinations of a chelating agent, anticoagulant, or antithrombotic agent, with an non-glycopeptide antimicrobial agent, such as the tetracycline antibiotics. Methods of using these compositions for coating a medical device and for inhibiting catheter infection are also disclosed. Particular combinations of the claimed combinations include minocycline or other non-glycopeptide antimicrobial agent together with EDTA, EGTA, DTPA, TTH, heparin and/or hirudin in a pharmaceutically acceptable diluent.

51 Claims, 11 Drawing Sheets

OTHER PUBLICATIONS

Condamine et al., "Acquired sideroblastic anaemia during treatment of Wilson's disease with triethylene tetramine dihydrochloride," *British Journal of Haematology*, 83:166–168, 1993.

Crosby and Gump, "Activity of Cefoperazone and Two b–Lactamase Inhibitors, Sulbactam and Clavulanic Acid, Against Bacteriodes spp. Correlated with b–Lactamase Production," *Antimicrobial Agents and Chemotherapy*, 22(3):398–405, Sep., 1982.

Dankert and Schut, "The antibacterial activity of chloroxylenol in combination with ethylenediaminetetra–acetic acid," *Journal of Hygiene*, 76(1):11–22, Feb., 1976 (Abstract).

Davis and Iannetta, "Influence of Serum and Calcium on the Bactericidial Activity of Gentamicin and Carbenicillin on *Pseudomonas aeruginosa*," *Applied Microbiology*, 23(4):775–779, Apr., 1972.

Delmotte et al., "Study of the sensitivity of pyocyanic bacillus (*Pseudomonas aeruginosa*) to antiseptics and antibiotics. IV. Synergism or antagonism between antiseptics [French]," *Therapie*, 27(3):445–455, May–Jun. 1972.

Diver et al., "The accumulation of five quinoline antibacterial agents by *Escherichia coli*," *Journal of Antimicrobial Chemotherapy*, 25:319–333, 1990.

Doss et al., "Effect of EDTA on Bacterial Resistance to antibiotics. A bacteriological and clinical study," *Journal of the Egyptian Medical Association*, 52(11):929–941, 1969.

Farca et al., "Potentiation of the in vitro activity of some antimicrobial agents against selected gram–negative bacteria by EDTA–tromethamine," *Veterinary Research Communications*, 17(2):77–84, 1993 (Abstract).

Fuursted, "Synergism and mechanism of subinhibitory concentration of streptomycin on *Streptococcus faecalis*," APMIS, 97:27–32, 1989.

Gerberick and Castric, "In Vitro Susceptibility of *Pseudomonas aeruginosa* to Carbenicillin, Glycine, and Ethylenediaminetetracetic Acid Combinations," *Antimicrobial Agents and Chemotherapy*, 17(4):732–735, Apr., 1980.

Gu and Neu, "In vitro Activity of Dactimicin, a Novel Pseudodisccharide Aminoglycoside, Compared with Activities of Other Aminoglycosides," *Antimicrobial Agents and Chemotherapy*, 33(11):1998–2003, Nov., 1989.

Hendrickson and Dunne, Jr., "Modification of Central Venous Catheter Flush Solution Improves In Vitro Antimicrobial Activity" *The Journal of Infectious Diseases*, 166:944–946, Oct. 1992.

Houlsby et al., "Effects of Preservatives, Steroids, and Ethylenediaminetetraacetate on the Antimicrobial Activity of Sulfacetamide," *Journal of Pharmaceutical Sciences*, 72(12):1401–1403, Dec., 1983.

Inman et al., "Determination of EDTA in vancomycin by liquid chromatography with absorbance rationing for peak identification," *Journal of Pharmaceutical & Biomedical Analysis*, 8(6):513–520 1990 (Abstract).

Knasmüller et al., "Investigations on the use of EDTA–permeabilized *E. coli* cells in liquid suspension and animal–mediated genotoxicity assays," *Mutation Research*, 216:189–196, 1989.

Kosmider et al., "Antibacterial action of complexing compounds. The influence of disodium versenate on microorganisms in vitro," *Archivum Immunologiae et Therapiae Experimentalis*, 20(6):931–937, 1972.

Light and Riggs, Jr., "Effect of Triethylenetetramine Dihydrochloride on the Antibiotic Susceptibility of *Pseudomonas aeruginosa*," *Antimicrobial Agents and Chemotherapy*, 13(6):979–984, Jun., 1978.

McMurry et al., "Susceptible *Escherichia coli* Cells Can Actively Excrete Tetracyclines," *Antimicrobial Agents and Chemotherapy*, 24(4):544–551, Oct., 1983.

Miyake et al., "Effects of etylenediaminetetraacetic acid and gentamicin on the antibacterial activity of pyridone carboxylic acid derivatives against Gram–negative bacilli," *Journal of Antimicrobial Chemotherapy*, 17:327–332, 1986.

Nezval and Ritzerfeld, "Antibacterial effect of the combination rifampicin–EDTA on *Pseudomonas* and *Proteus*," *Archiv fur Hygiene und Bakteriologie*, 153(6):548–551, Dec., 1969.

Nielsen and Close, "Edetate Disodium–Mediated Chloroamphenicol Resistance in *Pseudomonas cepacia*," *Journal of Pharmaceutical Sciences*, 71(7):833–834, Jul., 1982.

Nowakowska et al., "EDTA Disodium Salts as an Agent Modifying Penicillin Sensitivity of *Staphylococcus–Aureus* 1. Effect *In–Vitro* on Penicillin Resistant *Staphylococcus–Aureus*," *Med. Dosw. Mikrobiol.*, 34(1–2):7–12, (Abstract).

Nowakowska, "EDTA disodium salt as a factor modifying *Staphylococcus aureus* sensitivity to penicillin. II. Effect on *Staphylococcus aureus* in its various growth phases. [Polish]," *Med. Dosw. Mikrobiol.*, 34(1–2):17–26, 1982.

Rawal and Owen, "Combined Action of Sulfamethoxazole, Trimethoprim, and Ethylenediaminetetraacetic Acid on *Pseudomonas aeruginosa*," *Applied Microbiology*, 21(2):367–368, Feb., 1971.

Reid and Speyer, "Rifampicin Inhibition of Ribonucleic Acid and Protein Synthesis in Normal Ethylenediaminetetraacetic Acid–Treated *Escherchia coli*," *Journal of Bacteriology*, 104(1):376–389, Oct., 1970.

Richards, "Inactivation of resistant *Pseudomonas aeruginosa* by antimicrobial combinations," *J. Pharm. Pharmac.*, 23(Suppl.):136S–140S, 1971.

Rosen and Klebanoff, "Role of Iron and Etylenediaminetetraacetic Acid in the Bactericidial Activity of a Superoxide Anion–Generating Systems," *Archives of Biochemistry and Biophysics*, 208(2):512–519, May., 1981.

Radosz–Komoniewska et al., "Effects of disodium salt of ethylenediaminetetraacetic acid (Na2EDTA) and tetracyclines on drug resistant bacteria. Studies *in vitro*. [Polish], *Med. Dosw. Mikrobiol.*," 43(3–4):127–134, 1991 (Abstract).

Kapp–Burzynska et al., "Action in vitro of disodium ethylenediaminetetraacetic acid (Na2EDTA) and antibiotics on resistant strains of *Staphylococcus aureus* [Polish], *Med. Dosw. Mikrobiol.*," 45(2):153–158, 1993 (Abstract).

Seeger and Hentschel., "Der Influs von Äthylendiamintetraessigsäure auf die antibakterielle Aktivität einiger Antibiotics und ihre enterale Resorption beim Schwein," *Arzne-im.–Forsch.*, 10:1590–1594, 1971.

Weiser, "Combinations of Edtic Acid and Antibiotics in the Treatment of Rat Burns Infected with a Resistant Strain of *Pseudomonas aeruginosa*," *The Journal of Infectious Diseases*, 128(4):566–569, Oct., 1973.

Winstanley and Hastings, "Synergy between penicillin and gentamicin against enterococci," *Journal of Antimicrobial Chemotherapy*, 25:551–560, 1990.

Yamada et al., "Susceptibility of Micro–organisms to Active oxygen Species: Sensitivity to the Xanthine–oxidase–mediated Antimicrobial System," *Journal of General Microbiology*, 133:2007–2014, 1987.

Zietkiewicz et al., "Effect of EDTA combined with gentamicin on bacterial flora of burn wounds. [Polish]," *Polski Tygodnik Lekarski*, 40(32):904–906, Aug., 1985.

AHFS Drug Information, 1992 edition, Gerald K. McEvoy et al., editors, "Minocycline–HCl," pp. 318–319 and Edetate Disodium, pp. 1805–1807.

Anwar et al., "Interaction of Biofilm Bacteria with Antibiotics in a Novel In Vitro Chemostat System," *Antimicrobial Agents and Chemotherapy*, 33(10):1824–1826, 1989.

Anwar et al., "Tobramycin Resistance of Mucoid *Pseudomonas Aeruginosa* Biofilm Grown Under Iron Limitation," *Journal of Antimicrobial Chemotherapy*, 24:647–655, 1989.

Clumeck et al., "Treatment of Severe Staphylococcal Infectious with a Rifampicin–Minocycline Association," *Journal of Antimicrobial Chemotherapy*, 13(Suppl. C.):17–22, 1984.

Evans and Holmes, "Effect of Vancomycin Hydrochloride on *Staphylococcus Epidermidis* Biofilm Associated with Silicone Elastomer," *Antimicrobial Agents and Chemotherapy*, 31(6):889–894, 1987.

Farber et al., "*Staphylococcus Epidermidis* Extract Slime Inhibits the Antimicrobial Action of Glycopeptide Antibiotics," *Journal of Infectious Diseases*, 161:37–40, 1990.

Goodman and Gilman's *The Pharmacological Basis of Therapeutics*, Eighth Edition, Pergamon Press, Chapter 48, "Antimicrobial Agents," pp. 1117–1125, 1607–1608, 1990.

Harper and Epis, "Effect of Chlorhexidine/EDTA/Tris Against Bacterial Isolates from Clinical Specimens," *Microbios*, 51:107–112, 1987.

Hoyle et al., "The Biofilm Glycocalyx as a Resistance Factor," *Journal of Antimicrobial Chemotherapy*, 26:1–6, 1990.

Khoury and Costerton, "Bacterial Biofilms in Nature and Diseases," *Dialogues in Pediatric Urology*, 14(10):2–5, 1991.

Reid, Gregor, "Important Components in the Adhesion of Bacteria to Prosthetic Devices," *Dialogues in Pediatric Urology*, 14 (10):6–7, 1991.

Nickel, J. Curtis, "Bacterial Biofilms in Urological Infectious Diseases," *Dialogues in Pediatric Urology*, 14(10):7–8, 1991.

Machnicka et al., "Influence of 0.02 M EDTA and 3 M KCl on Surface of Hymenolepis Diminuta and Composition of Isolated Proteins, *Folia Histochemica Et Cytobiologica*," 24(1):65–70, 1986.

Marhshall, Kevin C., "Biofilms: An Overview of Bacterial Adhesion, Activity, and Control at Surfaces," *ASM News*, 58(4):202–207, 1992.

*The Merck Index: An Encyclopedia of Chemicals, Drugs, and Biologicals*, Eleventh Edition, Susan Budavari, Editor, Merck & Co., Inc., Publishers, Rahway, NJ, 1989, "Minocycline," p. 976.

Nickel et al., "Tobramycin Resistance of *Pseudomonas Aeruginosa* Cells Growing as a Biofilm on Urinary Catheter Material," *Antimicrobial Agents and Chemotherpy*, 27(4):619–624, 1985.

*Remington's Pharmaceutical Sciences*, 18th Edition, Alfonso R. Gennaro, Editor, Mack Publishing Company, Easton, PA, "Minocycline HCl," p. 1213, 1990.

Root et al., "Inhibitory Effect of Disodium EDTA upon the Growth of *Staphylococcus Epidermidis* in Vitro: Relation to Infection Prosphylaxis of Hickman Catheters," *Antimicrobial Agents and Chemotherapy*, 32(11) :1627–1631, 1988.

Said et al., "Expression of H 1 Outer–Membrane Protein of *Pseudomonas Aeruginosa* in Relation to Sensitivity to EDTA and Polymyxin B," *Journal of Medical Microbiology*, 24:267–274, 1987.

Solomon, Donald D., "Antibiotic Releasing Polymers," *Journal of Controlled Release*, 6:343–352, 1987.

Tojo et al., "Isolation and Characterization of a Capsular Polysaccharide Adhesin from *Staphylococcus Epidermisis*," *J. of Infect. Dis.*, 157 (4):713–722, 1988.

Vergeres and Blaser, "Amikacin, Ceftazidime, and Flucloxacillin Against Suspended and Adherent *Pseudomonas Aeruginosa* and *Staphylocuccus Epidermidis* in an In Vitro Model of Infection," *J. of Infect. Dis.*, 165:281–289, 1992.

Zinner et al., "Antistaphylococcal Activity of Rifampin with Other Antibiotics," *J. of Infect. Dis.*, 144(4):365–371, 1981.

Dialog Search Report printed in USA in 1992.

Yourassowsky et al., "Combination of Minocycline and Rifampicin against Methicillin–and Gentamicin–Resistant *Staphylococcus Aureus*," *J. Clin. Pathol.*, 34:559–563, 1981.

Segreti et al., "In Vitro Activity of Minocycline and Rifampin Against Staphylococci," *Diagn. Microbiol. Infect. Dis.*, 12:253–255, 1989.

Yuk et al., "Minocycline as an Alternative Antistaphylococcal Agent," *Review of Infectious Diseases*, 13:1023–1024, 1991.

Kamal et al., "Reduced Intravascular Catheter Infection by Antibiotic Bonding", *JAMA*, 265(18):2364–2368, 1991.

Raad et al., "Quantitative Tip Culture Methods and the Diagnosis of Central Venous Catheter–Related Infections", *Diagn. Microbiol. Infect. Dis.*, 15:13–20, 1992.

Sherertz et al., "Efficacy of Antibiotic–Coated Catheters in Preventing Subcutaneous *Staphylococcus aureus* Infection in Rabbits", *J. Infect. Dis.*, 167:98–106, 1993.

Sherertz et al., "Three–Year Experience with Sonicated Vascular Catheter Cultures in a Clinical Microbiology Laboratory", *J. Clin. Microbiol.*, 28(1):76–82, 1990.

International Search Report dated Nov. 12, 1993.

Hendrickson, et al., Department of Pediatrics, MACC Fund Research Center, Medical College of Wisconsin, Milwaukee, and Departments of Pathology and Pediatrics.

Kropec et al., "In Vitro Activity of Sodium Bisulfite and Heparin against Staphylococci: New Strategies in the Treatment of Catheter–Related Infection," *The Journal of Infectious Diseases*, 168:235–7, 1993.

Marmel et al., "Surface Antimicorbial Activity of Heparin––Bonded and Antiseptic–Impregnated Vascular Catheters," *The Journal of Infectious Diseases*, 167:920–4, 1993.

NON-GLYCOPEPTIDE ANTIMICROBIAL AGENTS IN COMBINATION WITH AN ANTICOAGULANT, AN ANTITHROMBOTIC OR A CHELATING AGENT, AND THEIR USES IN, FOR EXAMPLE, THE PREPARATION OF MEDICAL DEVICES

This application is a continuation in part of U.S. Ser. No. 08/150,472, filed Nov. 12, 1993 now abandoned, which was a continuation in part of U.S. Ser. No. 07/975,486, filed Nov. 12, 1992 now U.S. Pat. No. 5,362,754.

BACKGROUND OF THE INVENTION

1. Field of the Invention

The present invention relates to the field of indwelling medical devices, such as catheters, as well as to the field of methods and compositions for flushing and coating these medical devices. The field of the invention also relates to microbial-inhibiting pharmaceutical preparations. The invention also relates to pharmaceutical preparations useful in maintaining catheter patency and preventing infection. Methods of using the pharmaceutical preparation of the invention in the management and maintenance of a vascular catheter are also related to the present disclosure.

2. Background of the Related Art

Indwelling medical devices including vascular catheters have become essential in the management of hospitalized or chronically ill patients. Unfortunately, vascular catheters have become the major source for hospital-acquired sepsis. Hence, the benefit derived from indwelling medical devices such as vascular catheters is often upset by infectious complications. Thrombotic occlusions of the lumen of central venous catheters (CVC) is another complication that will often lead to the removal of catheters.

The current standard care of catheters includes flushing the lumen of the catheter with heparin. However, heparin has no antimicrobial activity. Thus, infections, as well as thrombotic occlusion, continue to occur frequently despite the prophylactic use of heparin flushes. Knowledge of the pathogenesis and microbiology of central venous catheter-related infections is essential in order to provide effective prevention for this problem.

Three essential factors must be considered in controlling for catheter colonization by infectious microbes. The first is controlling the availability of microorganisms that adhere to the inert catheter surface. Such microorganisms typically include staphylococci and candida. The second is control of the production of a slimy polysaccharide known as fibrous glycocalyx, by adherent microbial organisms. Production of the glycocalyx is essential for the adherence and integrity of these organisms. The third is control of the formation of the thrombin sheath by the host, which acts to engulf the catheter. The thrombin sheath provides the microorganisms a sticky substrate for enhanced adherence to the catheter, and thus, continued colonization and infection at the catheter site. The present inventors herein disclose solutions unique in their activity for inhibiting these conditions, and thus provide effective methods for controlling catheter-related infection and onset thereof.

*Staphylococcus epidermidis* and *S. aureus* account for 75% of CVC related infections. Candida species account for another 10% to 15% of such infections. The use of antistaphylococcal antibiotics to prevent these infections has been found to reduce CVC related bacterial infections, but only at the expense of the occurrence of higher rates of fungal (Candida) infections. The fibrous glycocalyx material produced by staphylococci and Candida helps these organisms adhere and stick to catheter surfaces, thus exacerbating the problem of eliminating these types of infections after they have become established. These microbial biofilm layers are made of fibrous glycocalyx material primarily polysaccharide in nature. The protective sheath provided by the glycocalyx at the infected site effectively prevents the elimination and treatment of these infections. Preparations effective for destroying such a glycocalyx would, therefore, provide a solution to treating established catheter infections where a glycocalyx has already been allowed to form.

Compositionally distinct glycocalyx material is produced by a variety of different organisms. For example, the glycocalyx produced by *Hymenolepis diminuta* is reportedly eliminated upon treatment with 0.02M. EDTA or 3M. KCl (Machnicka et al., 1986). However, the particular glycocalyx of *Hymenolepis diminuta* (tapeworm) is compositionally mostly proteins (Machnicka et al., 1986), which is distinct from the material of the glycocalyx typical of those organisms that colonize and cause catheter infection. For example, the glycocalyx of several staphylococcus species comprised primarily of polysaccharides with only low to nondeductible levels of protein (Tojo et al., 1988, in particular pg. 716, Table 1). Glycocalyx of microorganisms common to catheter infection are thus compositionally distinct from the organic composition of glycocalyx of such organisms as the tapeworm, *Hymenolepis diminuta*. A pharmaceutical preparation effective for reducing or eliminating glycocalyx of infectious microorganisms typically associated with catheter colonization and infection has yet to be identified.

Infectious microorganisms will typically embed themselves in the protective layer of the glycocalyx, thus providing a shield or hiding place that protects staphylococci and fungi from the activity of phagocytic cells. An agent or composition that would dissolve or prevent biofilm formation of these clinically important pathogens would thus provide a major breakthrough in the prevention of the typical catheter-related Staphylococcal and Candida infections that plague humans.

There has also been observed to be a correlation between thrombogenesis and infection. Essentially, indwelling vascular catheters get engulfed by a fibrin sheath that subsequently acts to cover the internal and external surfaces of a catheter. This fibrin sheath provides such organisms as Staphylococci and Candida, with an enhanced adherence capacity to the catheter surface. Unlike these particular microbes, gram-negative bacilli do not adhere well to fibrin and fibronectin. A composition that halted fibrin formation would thus be particularly useful in halting the colonization of Staphylococci, Candida, and the like, at indwelling catheter sites.

Intraluminal colonization through a catheter hub also constitutes a prelude to catheter-related infections and septicemias during long-term use of CVC. The inventors study presented herein of 359 long-term CVC patients (all of which were studied by quantitative catheter culture) demonstrates that CVCs with positive cultures, as well as matched negative controls, evidenced colonization (as quantitated by EM) and biofilm formation of the internal surface at least twice greater than that of the external surface of catheters that stayed longer than 10 days in place. This data is from nontunneled, noncuffed percutaneous CVC. For tunneled CVCs (Hickman/Robivac) and ports, internal colonization was even more prominent. The development of an anticoagulant pharmaceutical preparation effective against staphylococci, fungi, and polysaccharide-rich glycocalyx formation would thus provide a solution to the treatment and elimination of thrombogenesis and the septicemia associated with long-term CVC.

EDTA is an anticoagulant used in blood collection tubes. It is also recognized as a calcium chelating agent. EDTA is also recognized to have an antibacterial and antistaphylococcal effect (alone or in combination) (Harper & Epis, 1987; Said et al., 1987; Root et al., 1988). Root et al. (1988) compared the efficacy of EDTA for use with vascular catheters as an antibacterial agent to heparin alone and a vancomycin-heparin preparation in vitro. While those investigators found EDTA to be bacteriocidal, no remedy or suggestion of how the microbial glycocalyx of a device-related infection could be eliminated was provided. The effect of EDTA in combination with gentamicin has been described on bacterial flora of burn wounds (Zietkiewics et al., 1985). Miyake et al. (1986) described a reduction in the minimal inhibitory concentrations (MICs) of the pyridine carboxylic acid derivative antibiotics, nalidixic acid, cinoxacin and piromidic acid, when combined with EDTA or gentamycin. The MICs of piromidic acid, of loxacin and enoacin were unaffected by addition of EDTA or gentamycin.

Triethylene tetramine dihydrochloride (trientine 2HCl) (TTH) is another recognized chelating agent that chelates copper. It has been described for use in the treatment of Wilson's disease, an autosomal recessive disorder characterized by an accumulation of a toxic amount of copper in the body (Morita et al., 1992). Acquired sideroblastic anemia is a side effect reported with TTH treatment (Condamine et al., 1993).

Combination of dactimicin (a pseudo disaccharide aminoglycoside antibiotic) with EDTA has been observed to render *P. aeruginosa* susceptible to dactimicin treatment, while these bacteria were not observed to be susceptible to dactimicin in the absence of EDTA (Gu & Neu, 1989). EDTA treatment of enterococci has also been described as synergistically increasing the "killing curve" of gentamycin against these bacteria (Winstanley et al., 1990). Na2 EDTA has also been described in combination with oxytetracycline or doxycycline (Rudy et al., 1991).

The combination of rifampin with other antibiotics, in particular minocycline, has also been described (Clumeck et al., 1984; Yourassowsky et al., 1981; Zinner et al., 1981; Segreti et al., 1989; Yuk et al., 1991 and U.S. Pat. No. 5,217,493) for the treatment of severe staphylococcal infections.

EGTA (ethylene glycol-bis-[β-aminoethyl ether]-N,N,N', N'-tetraacetic acid) is another recognized chelating agent. This agent has not been described as antimicrobial or in combination with antibiotics. Other chelating agents, including TTH, and diethylenetriamine pentaacetic acid (DTPA), are known, but are similarly not recognized as having antimicrobial activity, or in compositions with antibiotics. Neither have these agents been described alone or in combination with antibiotics in treatment of catheter-related infections.

Although glycopeptide antibiotics (vancomycin and teicoplanin) are effective against staphylococci in vitro and in tissue, they are not active against adherent staphylococci embedded in a biofilm layer, such as glycocalyx. While flushing with such agents may acutely destroy these microorganisms, the risk of rapid development of tolerant and resistant strains in the patient being treated makes this a contraindicated procedure in most cases. In addition, there does not exist any well accepted treatment regimens for patients with vancomycin-tolerant or resistant strain bacteremias, thus leaving this patient population without an antibiotic that could be used therapeutically.

Based on all of the above, the ideal prophylactic agent for catheter maintenance would both inhibit/eliminate the formation of polysaccharide-rich glycocalyx and eliminate staphylococci and fungi.

It is an object of the invention to provide a composition having both an anti-staphylococcal and antifungal (anti-Candida) activity effective against free-floating and adherent organisms embedded in biofilm as well as having activity against other microorganisms that may cause foreign body infections. It is a further object of the invention to provide an anticoagulant agent and/or method that would prevent and alter/dissolve a polysaccharide-rich fibrous glycocalyx biofilm layer. Such a pharmaceutical agent would optimally provide an anticoagulant that would prevent thrombotic occlusion of the catheter lumen as well as thrombin formation. Additional objects of the invention include providing an agent that could be given intraluminally without a toxicity concern to humans and to provide methods that would kill adherent staphylococci and Candida. Such methods would preferably not include the use of the same or similar agents that a clinician would use therapeutically (such as Vancomycin, Ampho B, or Azoles).

The present invention demonstrates that a mixture of particular non-glycopeptide antibiotics and selected chelating and antithrombotic agents, do fulfill the listed objects.

SUMMARY OF THE INVENTION

The present invention provides unique and effective pharmaceutical compositions that include effective amounts of a non-glycopeptide antimicrobial agent, such as a non-glycopeptide antibiotic or antifungal agent, and a chelating agent, anticoagulant or antithrombotic agent. In one preferred embodiment, the chelating agent is EDTA and the non-glycopeptide antimicrobial agent is minocycline. In other embodiments, the composition comprises a non-glycopeptide antimicrobial agent and an anticoagulant, an antithrombotic agent, or a chelating agent other than EDTA. A preferred combination includes a non-glycopeptide antimicrobial agent and a calcium chelating agent, such as EGTA. Chelating agents that may be used in conjunction with the present invention include EDTA (ethylenediaminetetraacetic acid), EGTA, DTPA (diethylenetriamine pentaacetic acid), DMSA, deferoxamine, Dimercaprol, edetate calcium disodium, triethylene tetramine dihydrochloride, zinc citrate, combination of bismuth and citrate, penicillamine, succimer and Editronate. Other preferred chelating agents include those that chelate divalent metal cations such as Ca, Mg, Mn, Fe and Zn.

The compositions of the invention preferably also include a pharmacologically acceptable carrier solution, such as water, Ringers solution or saline.

Chelating agents represent a very important aspect of the present invention. A wide variety of chelating agents are currently known may be used in the mixtures of the present invention.

In particular embodiments of the invention, EDTA is the chelating agent for in a kit with minocycline. However, it is understood that one may exclude EDTA from the various compositions and devices and still maintain the desired therapeutic benefits of the present invention.

The chelating agent of the compositions preferably provides potent glycocalyx inhibiting potential. Non-glycopeptide antimicrobial agents of the compositions, such as minocycline at high concentrations, preferably have a fungicidal effect and a unique ability to penetrate a polysaccharide-rich glycocalyx biofilm layer. The combination of the non-glycopeptide antimicrobial agent and chelating agent provides a unique combination anticoagulant, anti-microbial, glycocalyx inhibiting, antibacterial and antifungal agent for the prevention of thrombogenesis, microbial adherence and device-related infections. Minocycline-EDTA is one example of such a combination that may be preferred for use in a kit. Chelating agents other than EDTA that are desired include in particular EGTA.

Antimicrobial agents that may be used in conjunction with the present invention include the non-glycopeptide antibiotics, such as the tetracyclines. Examples of the tetracyclines that may be used in combination with the selected chelating agents include immunocycline chlortetracycline, oxytetracycline, demeclocycline, methacycline and doxycycline.

Additional antibiotics, such as the rifamycins, particularly rifampin, may also be used together in the preparation of the claimed compositions of chelating agents and non-glycopeptide antimicrobial agents, as contemplated by the present inventors.

Another preferred embodiment of the claimed compositions comprises an anticoagulant and an antimicrobial agent, preferably a non-glycopeptide antimicrobial agent such as the tetracycline antibiotics. Preferred anti-coagulants include heparin, low molecular weight heparin, a combination of citrate and heparin, enoxaparin sodium, coumarin and indanedione derivative, anisindione, warfarin, protamine sulfate, streptokinase, urokinase, anti-thrombin III, and atlephase recombinant, anistreplase. By way of example, useful tetracycline antibiotics include minocycline, doxycycline and oxytetracycline. These compositions may further include a rifamycin, such as rifampin.

Still another embodiment of the claimed compositions comprise the anticoagulant, hirudin and an antimicrobial agent, preferably a non-glycopeptide antimicrobial agent. The antimicrobial agent is most preferably a tetracycline antibiotic, such as minocycline, doxycycline, or oxytetracycline. These compositions may further include a rifamycin antibiotic, such as rifampin.

Other embodiments of the claimed compositions may include a combination of a chelating agent, a non-glycopeptide antimicrobial agent, and heparin. An example of such a combination is EDTA, minocycline, and heparin. These compositions may also include rifamycin. By way of example, such a combination would include EDTA, minocycline, heparin and rifampin. However, where one may choose to exclude EDTA, many other chelating agents and antimicrobial agents together with heparin and rifampin may also be used in the practice of the present invention.

The inventors have shown that minocycline's penetration of the microbial biofilm layer is at least 6-fold higher than vancomycin. The inventors also demonstrate that the particular amounts of EDTA employed in the detailed Examples are unique in effectively preventing and dissolving polysaccharide-rich microbial glycocalyx. Where one may choose to exclude EDTA, other chelating agents are also expected to provide this observed activity, particularly together with an antibiotic, such as the tetracycline family of antibiotics.

The invention in still another aspect provides methods of using compositions of the chelating agent, anticoagulant or antithrombotic agent mixture with non-glycopeptide antimicrobial agents in a variety of therapeutic applications. One such therapeutic application is for preventing catheter infections. An example of a composition to be used in the practice of these methods comprises minocycline together with a chelating agent, anticoagulant or antithrombotic agent. EDTA is an example of a chelating agent contemplated for use in these methods, however, other chelating agents would also be expected to be useful. Minocycline is demonstrated to kill adherent staphylococci embedded in glycocalyx (Example 4). In this regard, minocycline is demonstrated by the present inventors to be superior to vancomycin, a glycopeptide antibiotic. Vancomycin is currently the standard antibiotic used in the treatment of *Staphylococcus epidermidis* and resistant *Staphylococcus aureus*.

Particularly preferred preparations of the present invention comprise a mixture of a pharmacologically effective amount of minocycline and EDTA, EGTA, triethylene tetramine dihydrochloride, DTPA, hirudin, or heparin in a pharmacologically acceptable carrier solution, either alone or together with rifampin or other rifamycin antibiotic.

For use in maintaining catheter patency, the pharmaceutical preparation of the invention may be efficaciously used with such medical devices as a central venous catheter, a peripheral intervenous catheter, an arterial catheter, a Swan-Ganz catheter, a hemodialysis catheter, an umbilical catheter, a percutaneous nontunneled silicone catheter, a cuffed tunneled central venous catheter as well as with a subcutaneous central venous port.

The invention also provides for medical devices, such as catheters, that are coated with any of the mixtures of chelating agents, antithrombotic agents, or anticoagulants, together with a non-glycopeptide antimicrobial agent. The mixture in one preferred embodiment comprises EDTA and minocycline. Where the chelating agent is other than EDTA, the mixture in one example includes EGTA together with an antimicrobial agent, such as a tetracycline antibiotic. Particular exemplary medical devices that may be prepared and coated with the preparations of the present invention are provided in the above list.

The present invention also provides for particular processes for preparing the coated medical devices with the compositions described herein. In a most preferred embodiment, the process comprises exposing the medical device to a composition of a chelating agent, an anticoagulant, or antithrombotic agent combined with a non-glycopeptide antimicrobial agent for a sufficient amount of time to provide a coating on the exposed surface of the device. Where the composition is in a liquid form, it would be allowed to dry on the surface of the device so as to form a film.

In a preferred embodiment of the above described methods and processes, the device is first treated with a surfactant before exposing the device to the composition. Such surfactants, by way of example, include tridodcylmethyl ammonium chloride and benzalkonium chloride.

For the herein described uses, a combination of a non-glycopeptide antimicrobial agent, particularly a tetracycline antibiotic, and chelating agent, may be prepared containing a concentration of between about 0.001 to about 1,000 mg/ml, or preferably between about 1 to about 200, or from about 10 to about 100 mg/ml of the chelating agent (preferably between about 20 to about 100 or about 20 to about 60 mg/ml), and between about 0.001 to about 1000 mg/ml (preferably between about 1 to about 200, or from about 2 to about 100 mg/ml) of the non-glycopeptide antimicrobial agent (preferably between about 10 to about 100, or about 2 to about 9 mg/ml). Most preferably, the preparation includes about 30 mg/ml of the chelating agent and about 3 mg/ml of the non-glycopeptide antimicrobial agent.

Where minocycline is the antimicrobial agent of choice, it may be reconstituted to an appropriate concentration from a 100 mg vial of minocycline and then combined in the manner described herein (Minocin® Intravenous, Lederle, Carolina, Puerto Rico) to provide a preparation with the concentration of minocycline desired according to methods well known to those of ordinary skill in the art of pharmaceutical preparations. The carrier solution, by way of example, may comprise saline, phosphate buffered saline, dextrose in water, Ringers solution or water.

In one particular aspect of the invention, a catheter flushing pharmaceutical preparation is provided. Most preferably, the catheter flushing pharmaceutical preparation comprises a glycocalyx inhibiting concentration of the chelating agent, anticoagulant or antithrombotic agent, and an effective amount of a non-glycopeptide antimicrobial agent, in a pharmaceutically acceptable carrier solution (e.g., saline). More specifically, the concentration of the chelating agent in one embodiment of the preparation is between about 0.001 mg/ml to about 1,000 mg/ml, or between about 1 to about 200, or even more preferably between about 10 to about 100 mg/ml. The concentration of the antimicrobial agent most preferred is between about 0.001 mg/gl to about 1,000 mg/ml or between about 1 to about 200 mg/ml, or even more preferably between about 2 to about 100 mg/ml or between about 2 to about 9 mg/ml, in the preparation. In one preferred embodiment of the preparation, the chelating agent is EGTA and the non-glycopeptide antimicrobial agent is the antibiotic, minocycline.

Another embodiment of the catheter flushing pharmaceutical preparation of the invention may be described more particularly as including about 30 mg/ml EDTA and about 3 mg/ml minocycline. By way of example, the carrier solution is saline, water, or a Ringers solution. The catheter flushing preparation of the present invention may advantageously be used to inhibit the formation of polysaccharide-rich glycocalyx. In this manner, infections characterized by such a formation may be effectively eliminated.

A "glycocalyx inhibiting concentration" is defined for purposes of describing the present invention as a concentration effective to degrade, dissolve, or otherwise inhibit a polysaccharide-rich glycocalyx. By way of example, such a polysaccharide-rich glycocalyx is characteristic of established staphylococcal infections of S. aureus and S. epidermidis.

Another aspect of the present invention provides a method of preparing a biofilm-resistant medical device. The method in one embodiment comprises exposing a device with the compositions or catheter flushing preparations described herein. Any of a variety of catheters may be treated or coated according to the described method employing coating techniques well known to those of ordinary skill in the art.

While the method may be used to coat virtually any surface where glycocalyx formation is to be desirably inhibited, use of the method in preparing a microbial biofilm-resistant catheter device is particularly envisioned. By way of example, catheters that may be prepared and treated according to the invention include a central venous catheter and a triple lumen catheter. It is anticipated that the method will provide a device resistant to polysaccharide-rich glycocalyx formation, such as that typical of Staphylococci.

In a preferred aspect of the described method, a biofilm-resistant medical device is prepared using a pharmaceutical preparation of a chelating agent, anticoagulant, or antithrombotic agent and a non-glycopeptide antimicrobial agent. An example of such preparation comprises a combination of minocycline and EDTA, or a combination of a chelating agent other than EDTA, antithrombotic or anticoagulant agent together with a non-glycopeptide antimicrobial agent. Examples of the latter preparations are provided at Example 25, and include the combination of EGTA and minocycline. The various concentration ranges of the non-glycopeptide antimicrobial agents and chelating agents described above are also contemplated as useful in the compositions for coating a medical device. Other concentration ranges include between about 10 mg/ml and about 200 mg/ml of the non-glycopeptide antimicrobial agent and between 10 mg/ml and about 200 mg/ml of the chelating agent, anticoagulant, or antithrombolic agent. One embodiment of the method comprises use of a composition that includes about 60 mg/ml of the non-glycopeptide antimicrobial agent and about 60 mg/ml of the chelating agent. Antimicrobial agents that are specific examples for use in these methods include the tetracycline antibiotics, such as minocyline, doxycycline, or oxytetracycline.

The method in one aspect comprises preparing a pharmaceutical preparation of the desired combination in a biocompatible adherent coating carrier solution. The surface of the medical device of interest is then exposed to the pharmaceutical preparation for a period of time sufficient to allow the formation of a film or coating of the preparation on the surface of the device. This may be accomplished, for example, by dipping the device in the preparation. Most preferably, the device to be coated is a catheter. Such treatment provides a biofilm-resistant catheter.

The pharmaceutical preparation of the method in a particularly preferred embodiment is further described as comprising about 3 mg/ml of the antibiotic, such as minocycline, and about 30 mg/ml of the chelating agent or anticoagulant, such as EDTA, EGTA or DTPA.

As used in the description of the present invention, a "biofilm-resistant" device or surface is defined as a surface or device that will prevent the adherence or growth of organisms that produce polysaccharide-rich glycocalyx material. Such organisms include the Staphylococcal aureus and epidermidis species. However, any organism that produces a polysaccharide-rich glycocalyx material would be equally inhibited by the herein described devices, surfaces and pharmaceutical preparations.

The present invention also provides a method for inhibiting glycoprotein-rich glycocalyx formation at a catheter port. The method in one embodiment comprises flushing the catheter periodically with a pharmaceutical preparation comprising a glycocalyx-inhibiting concentration of a chelating agent, an anticoagulant or an antithrombotic agent, and a non-glycopeptide antimicrobial agent, in a pharmacologically acceptable carrier solution. In one aspect of the method, the composition includes a chelating agent defined as EDTA, EGTA, DTPA or TTH. In particular embodiments, the chelating agent is included in the composition at a concentration of between about 0.001 to about 1,000 mg/ml, or preferably between about 1 to about 200, or between about 10 to about 100 mg/ml. In preferred embodiments, between about 20 to about 60 mg/ml of the chelating agent is included in the flushing solution. A preferred concentration of the chelating agent in the composition is about 30 mg/ml. Where minocycline is the non-glycopeptide antimicrobial agent, a glycocalyx inhibiting concentration may be defined as between about 0.001 mg/ml and about 1,000 mg/ml (preferably between about 1 to about 200, 2–100, most preferably between about 2 and about 9 mg/ml). A preferred concentration of antimicrobial agent to use is about 3 mg/ml. Other non-glycopeptide antimicrobial agents may also be used, such as doxycycline or oxytetracycline.

The described method may be used to inhibit infection at virtually any tunneled or untunneled catheter. As part of a catheter maintenance regimen, the catheter most preferably is to be flushed with a composition comprising a non-glycopeptide antibiotic and a chelating agent, anticoagulant or antithrombotic agent, in a pharmaceutically acceptable carrier solution. The aforedescribed preparation once a week, once every 4 days, once every 2 days, once a day (about every 24 hours), twice a day, every four hours or as needed according to patient needs.

In still another aspect of the invention, a method for eliminating microbial glycocalyx formation, particularly polysaccharide-rich (Staphylococcal) glycocalyx formation, at a catheter lumen is provided. The method, in one embodiment, comprises preparing a solution comprising a chelating, anticoagulant or antithrombotic agent, together with a non-glycopeptide antimicrobial agent, (such as a tetracycline antibiotic, minocycline and EDTA, EGTA, or both are a preferred combination), in a carrier solution to provide a flushing composition, and flushing the catheter with a therapeutically effective amount of the flushing composition.

Specific combinations preferred for use as a flushing composition are described in example 25. In one embodiment, the flushing composition is an M-EDTA preparation that includes a concentration of minocycline of between about 0.001 to about 1,000 mg/ml (preferably between about 2 to about 9 mg/ml) and between about 10 to about 100 mg/ml (preferably between about 20 to about 60 mg/ml) EDTA. The therapeutically effective amount of the aforedescribed M-EDTA preparation would, therefore, constitute between about 1–10 ml (preferably about 2–3 ml) of the solution in a most particularly preferred embodiment of the flushing preparation.

Most preferably, the catheter will be flushed with a volume of about 3 ml of the aforedescribed M-EDTA preparation containing about 30 mg/ml EDTA and about 3 mg/ml minocycline. The catheter is to be flushed periodically at intervals of once a week, once every 4 days, once every 2 days, once a day, twice a day, every four hours, or as needed according to patient needs, with between about 2–3 ml of the M-EDTA preparation. The catheter flushing regimen may simply constitute once every time that the catheter is changed. In a preferred aspect of the method, the catheter is to be flushed more frequently at 4 hour intervals with the herein described preparations.

The compositions of the present invention are expected to remain therapeutically effective for use as a catheter-flushing agent stored at a refrigerated temperature. Preparations of the flushing compositions have remained effective for at least 1 month after formulation when stored under refrigerated conditions. In addition, the M-EDTA solution should be brought to room temperature before use on an animal or patient.

The present invention in still another aspect provides a kit. In one embodiment, the kit comprises a container means, such as a compartmentalized syringe, that comprises at least three separate compartment means. Where there are 3 compartments, one compartment comprises a non-glycopeptide antimicrobial agent, such as minocycline; the second container means comprises a chelating agent, such as EDTA, an anticoagulant or an antithrombotic agent (e.g., heparin or hirudin). The third container means comprises a diluent, such as saline, Ringers solution, or water. Kits that include a carrier means adapted to receive at least two container means constitute still another embodiment of the kit. In these embodiments, the chelating agent, antithrombotic agent, or anticoagulant, would be included together with the non-glycopeptide antimicrobial agent within a first container means (i.e., compartment of the device). The second container means would comprise a diluent, such as the ones described above. In a preferred aspect, the chelating agent and antimicrobial agent are included together in a container means of the device in dry powder form. The dry components would preferably be combined with the diluent of the second container means to provide a solution suitable for use.

In these various embodiments, the kit preferably includes a chelating agent. In particular embodiments, the chelating agent is EDTA, and the non-glycopeptide antimicrobial agent is preferably an antibiotic. By way of example, such an antibiotic is minocycline.

The aforedescribed compositions and preparations are expected to be effective in preventing the adherence and colonization of catheter surfaces by *S. aureus, S. epidermidis*, and fungi, as well as effective in both treating and eliminating already formed glycocalyx formations of these infectious organisms.

The following abbreviations are used in the description of the present invention:

CVC=Central Venous Catheters
MRD=Modified Robbins Device
M-EDTA=minocycline-EDTA mixture
$D_{10}/W$=10% Dextrose and Water

DETAILED DESCRIPTION OF THE PREFERRED EMBODIMENTS

Figure 1:
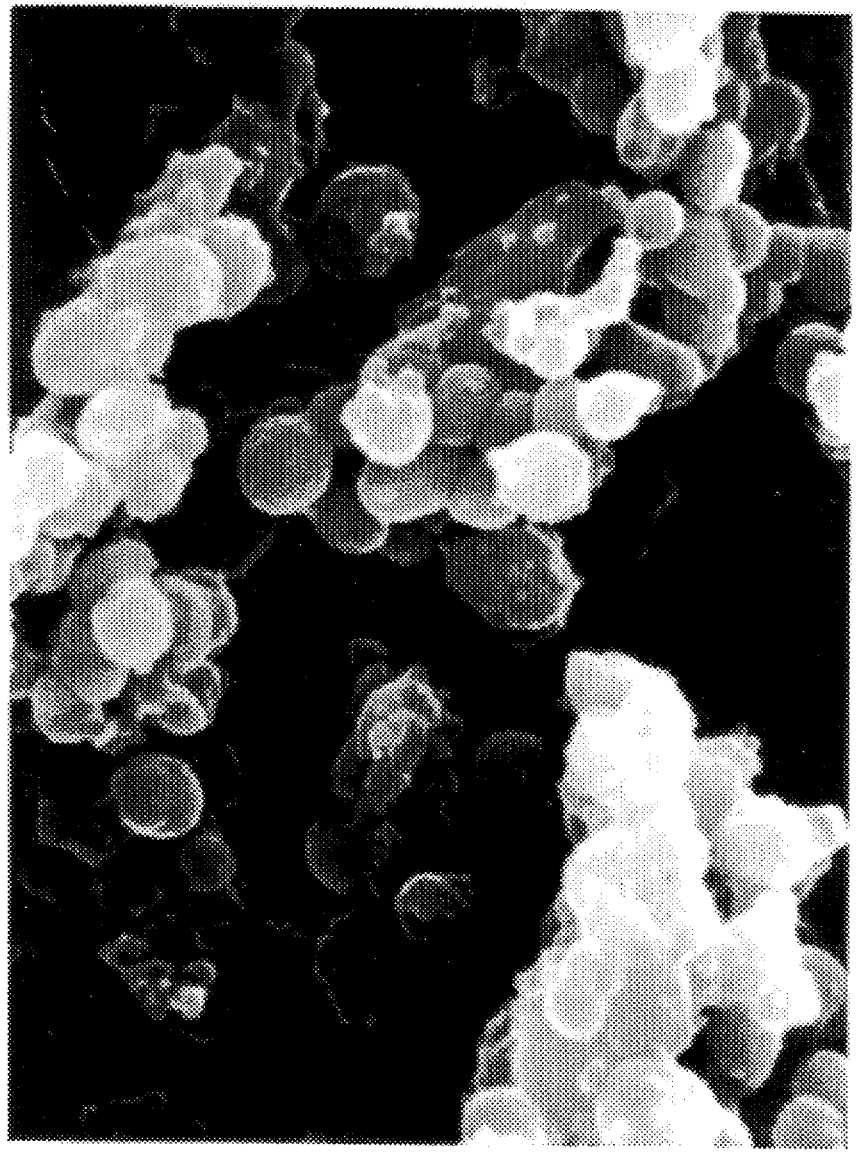
FIG. 1 Scanning electron microscopy picture showing staphylococci and biofilm from a control catheter segment that was exposed to slime producing *S. epidermidis* and later immersed in Dextrinase for 24 hours. (Example 6 results.)

The present invention provides pharmaceutically effective compositions of non-glycopeptide antimicrobial agents and chelating agents, anticoagulants or antithrombotic agents. These compositions are expected to be particularly useful in preventing the formation of the "biofilm" or polysaccharide-rich glycocalyx that typically accompanies microbial surface colonization. In particular, the compositions are expected to be most effective in breaking down staphylococcal glycocalyx and in inhibiting its formation. This feature renders the compositions of the present invention particularly useful in the treatment of staphylococcal infections where a polysaccharide-rich glycocalyx has formed or may potentially be formed, as well as in the prevention and treatment of Staphylococcal and Candida infection.

The present invention also provides treated or coated medical devices, such as catheters, that prevent staphylococcal or fungal colonization. The coating or film provided on these devices comprises a non-glycopeptide antimicrobial agent, such as a tetracycline antibiotic, and a chelating agent, antithrombotic agent or anticoagulant. A particular combination of ingredients of the claimed compositions include minocycline and EDTA. Other preferred combinations of the invention comprise a glycocalyx inhibiting concentration or amount of a non-glycopeptide antimicrobial agent and an anticoagulant or a chelating agent other than EDTA. Specific combinations are provided in Example 25. Devices coated with any of these combinations of agents are also envisioned to be useful as part of the present invention.

Kits designed to provide the compositions and preparations of the present invention are also described.

The minocycline used in the studies described in the present disclosure was obtained from Lederle (Minocin® (intravenous, 100 mg, Carolina, Puerto Rico). The disodium-EDTA used in the studies described in the present disclosure was obtained from Abbott Co. (Endrate® (Intravenous 150 mg/ml) Chicago, Ill.) A Modified Robbin's Device, a screening tool customarily used and accepted as predictive of catheter use in humans (Nickel et al., 1985; Evans & Holmes, 1987), was used in the present study of the M-EDTA pharmaceutical preparations. The model was constructed at M. D. Anderson Cancer Center in Houston, Tex.

The following agents were used in the studies disclosed herein:

| SUBSTANCE | BRAND NAME | SOURCE | LOCATION |
| --- | --- | --- | --- |
| Urokinase | Abbokinase | Abbott Laboratories | Chicago, IL |
| Heparin | — | Sigma Chemical | St. Louis, MO |

-continued

| SUBSTANCE | BRAND NAME | SOURCE | LOCATION |
| --- | --- | --- | --- |
| Saline | 0.09 Sodium Chloride (injection U.S.P.) | Baxter Healthcare Corp. | Deerfield, IL |
| Dextrinase | — | Sigma Chemical Co. | St. Louis, MO |
| Vancomycin | Lyphocin Intravenous, 1 gram | Lyphomed | Rosemont, IL |
| Trypticase Soy broth | — | DIFCO Laboratories | Detroit, MI |

Even though the invention has been described with a certain degree of particularity, it is evident that many alternatives, modifications, and variations will be apparent to those skilled in the art in light of the present disclosure. Accordingly, it is intended that all such alternative, modifications, and variations which fall within the spirit and the scope of the invention be embraced by the defined claims.

The following examples are presented to describe preferred embodiments and utilities of the present invention, but should not be construed as limiting the thereof.

It should be appreciated by those of skill in the art that the technique disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiment which are disclosed and still obtain like or similar results without departing, again, from the spirit and scope of the present invention.

EXAMPLE 1

Preparation of M-EDTA Pharmaceutical Preparation

The present example provides a detailed description of how the M-EDTA pharmaceutical preparation is to be prepared. EDTA was obtained from Sigma. The minocycline was obtained from Lederle.

The M-EDTA solution was prepared as follows so as to achieve a concentration of about 3 mg/ml minocycline and about 30 mg/ml EDTA in a sterile saline solution. Separate solutions of EDTA (60 mg/ml) and minocycline (3 mg/ml) were prepared in saline. The EDTA was reconstituted from 200 mg/ml Edetate Calcium Disodium (Versenste®, 3M Riker, Northridge, Calif.) or reconstituted from Edetate Disodium (150 mg/ml parenteral concentrate (Endtrate®, Abbott, Chicago, Ill., or Disotate®, Forest, Md. Heights, Mo.). Alternatively, the 60 mg/ml of EDTA could be reconstituted from EDTA powder (Sigma Chemical Co., St. Louis, Mo.). Minocycline was obtained from Lederle and combined with a volume of saline sufficient to constitute about 3 mg/ml minocycline.

The 6 mg/ml minocycline and 60 mg/ml EDTA solutions were mixed in equal volumes to constitute a 3 mg minocycline and 30 mg EDTA/ml solution. The solution was then brought to a physiologically acceptable pH of about 7.4. The solution was stored in a sterile container.

Figure 11A:
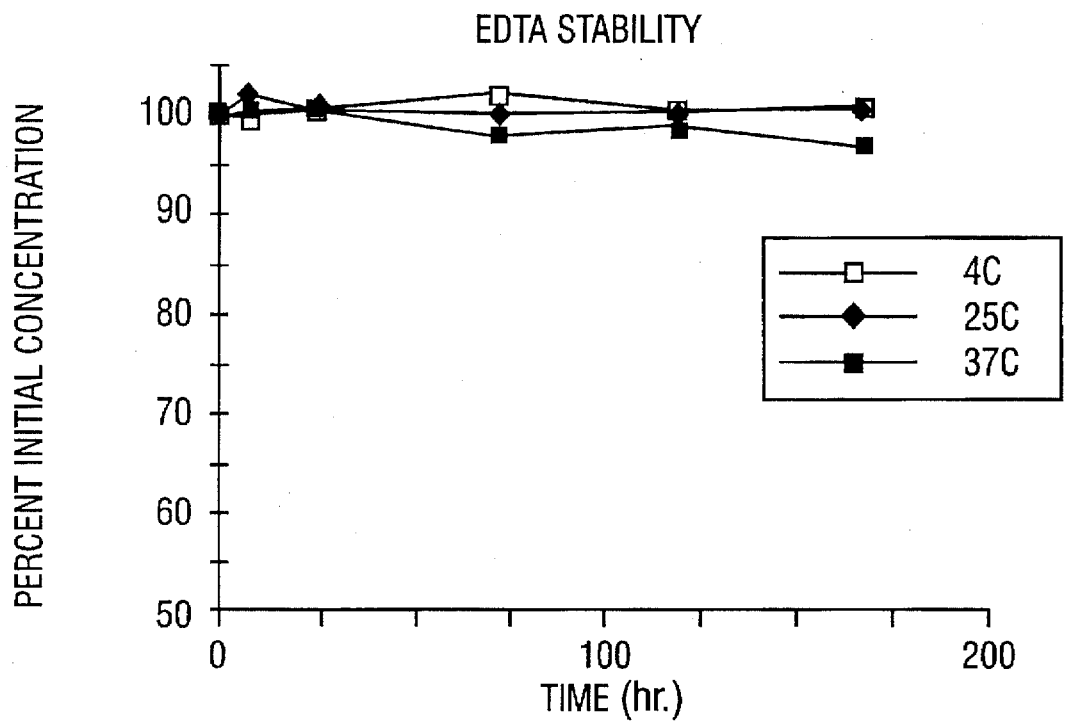
FIG. 11(A) EDTA Stability
Figure 11B:
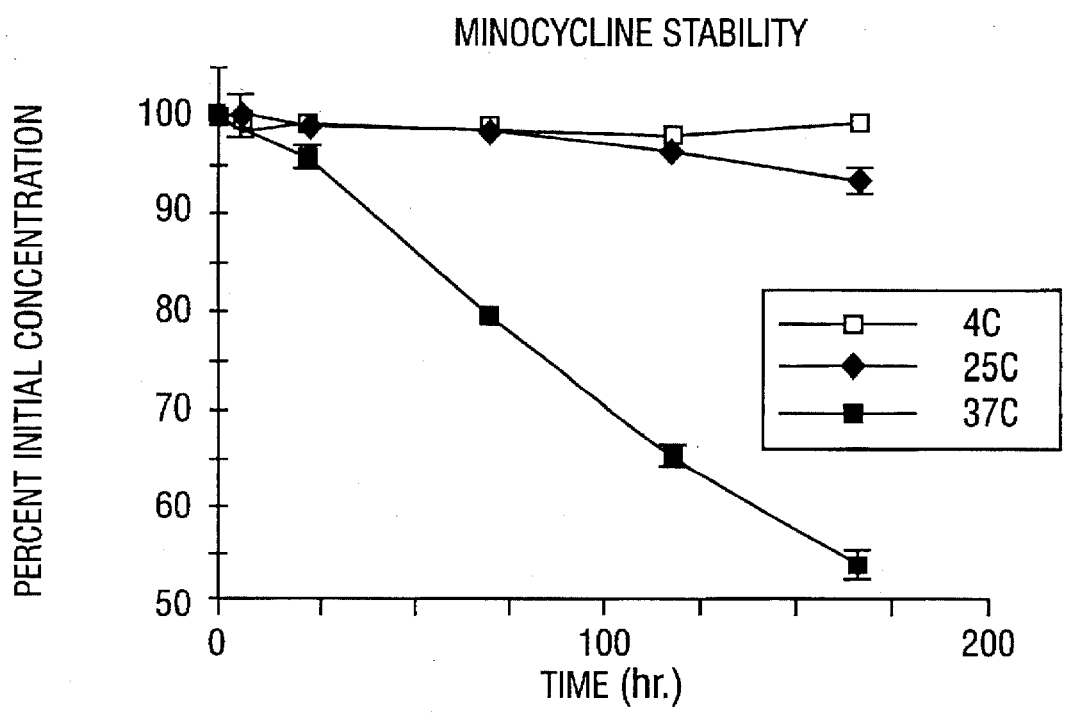
FIG. 11(B) Minocycline Stability

Once formulated, the M-EDTA may be stored refrigerated at 4° C. until use. It is contemplated that so formulated, the solution will remain chemically stable and pharmacologically active for at least 1 month at 4° C. The preparation is also very stable at room temperature (37° C.) for at least 72 hours (Table 1 and FIG. 11). The preparation should be at room temperature before administration to a patient or animal.

Once formulated, the M-EDTA may be stored refrigerated at 4° C. until use. It is contemplated that so formulated, the solution will remain chemically stable and pharmacologically active for at least 1 month at 4° C. The preparation is also very stable at room temperature (37° C.) for at least 72 hours (Table 1 and FIG. 11). The preparation should be at room temperature before administration to a patient.

inhibiting *S. epidermidis* adhesion and glycocalyx formation at a catheter surface.

Catheter segments were placed in the specimen plugs of the Modified Robbins Device described in Example 2. After placing the catheter segments in the specimen plugs, the entire apparatus was sterilized with ethylene oxide. A 500 ml 10% dextrose/water bag was infected with $4 \times 10^8$ CFU/ml of *S. epidermidis* (to produce $8 \times 10^5$ CFU per ml of $D_{10}$/W). The infected infusate was flushed through the MRD for 3 hours at a 50 ml/hr (using a peristaltic pump). In order to remove all free floating and loosely adherent staphylococci, the infected bag was removed and a new sterile bag (of

TABLE 1

Percentage of Initial Concentration Remaining* of Calcium Disodium Versenate (EDTA) 30.0 mg/mL and Minocycline Hydrochloride 3 mg/mL in a Catheter Flushing Solution. Detected by High Power Liquid Chromatography.

| Temperature (C) | Storage time (hr) | | | | | |
|---|---|---|---|---|---|---|
| | 0 | 6 | 24 | 72 | 120 | 168 |
| EDTA | | | | | | |
| 37 | 100.0 ± 0.5 | 99.9 ± 0.6 | 100.3 ± 0.2 | 97.9 ± 0.4 | 99.0 ± 0.5 | 96.9 ± 0.2 |
| 25 | 100.0 ± 0.5 | 102.1 ± 0.3 | 100.9 ± 0.0 | 100.1 ± 0.1 | 100.4 ± 0.2 | 100.5 ± 0.2 |
| 4 | 100.0 ± 0.5 | 100.2 ± 0.1 | 100.8 ± 0.2 | 101.7 ± 0.8 | 100.3 ± 0.1 | 100.9 ± 0.4 |
| Minocycline Hydrochloride | | | | | | |
| 37 | 100.0 ± 0.2 | 99.76 ± 0.0 | 96.0 ± 1.3 | 79.9 ± 0.7 | 65.4 ± 1.0 | 53.5 ± 1.3 |
| 25 | 100.0 ± 0.2 | 100.5 ± 19 | 99.4 ± 0.8 | 98.7 ± 0.5 | 96.8 ± 0.5 | 93.8 ± 0.6 |
| 4 | 100.0 ± 0.2 | 98.9 ± 0.4 | 99.7 ± 0.5 | 98.8 ± 0.7 | 98.3 ± 0.6 | 99.8 ± 0.1 |

*Mean of duplicate determinations ± S.E.M.

EXAMPLE 2

Description of the In Vitro Model

The present example is provided to describe the study model employed for illustrating the antimicrobial and therapeutic utility of the minocycline and EDTA preparations of the present invention.

An in vitro model consisting of the Modified Robbin's Device (MRD) was used to study the formation of biofilm and colonization of catheter segments of *S. epidermidis*. This is a well established model that is described in Nickel et al. (1985) and Evans & Holmes (1987), and provides a study model recognized by those of skill in the art as predictive of in vivo effects at a catheter surface.

The MRD is constructed of an acrylic block, 42 cm long, with a limen of 2×10 mm. The MRD is made of twenty-five evenly spaced specimen plugs each connected to a catheter latex segment whose anterior surface (0.3 cm$^2$) comes in contact with the flushed infusate coming from a connected tubing and infusion bag. Several studies were conducted using this model, which are outlined in the following examples.

EXAMPLE 3

Inhibition of *S. epidermidis* In Vitro

The present example is provided to demonstrate the utility of the present invention for inhibiting *S. epidermidis* in and on a catheter. The in vitro model described in Example 2 was used in the study. The present example will demonstrate the utility of the present invention for the treatment and maintenance of catheter patency in vivo, and more specifically for $D_{10}$/W) was used to flush the MRD. The MRD was flushed with sterile $D_{10}$/W for 24 hours at 40 mls/hr. Following this, catheter segments of equal size were treated with different agents by placing them in tubes containing one of the following solutions:

1. Urokinase (5000 units/ml);

2. Heparin (1000 unit/ml);

3. EDTA (50 mg/ml); and

4. Trypsin (20,000 units/ml).

Representative catheter segments were then removed (in a sterile manner) at 4 and 24 hours and quantitatively cultured using the scrape-sonication technique described by Khoury & Costerton (1991) to isolate organisms adherent to catheter surfaces. The Khoury & Costerton (1991) reference is specifically incorporated herein by reference for this purpose. The experiment was done at 37° C.

The results from this study are presented at Table 2. The results demonstrate that treatment of catheter surfaces with EDTA was effective in preventing adherent *S. epidermidis* colonies on a catheter surface after only 4 hours of treatment. In contrast, urokinase, heparin and trypsin treatment of the catheter segments was significantly less effective at inhibiting adherent *S. epidermidis* colony formation and adherence after 4 hours of treatment.

TABLE 2

| Agent | No. of adherent *S. epidermidis* colonies obtained from 0.3 cm² catheter surfaces | |
|---|---|---|
| | After 4 hrs. of treatment | After 24 hrs. of treatment |
| Urokinase | 310 | 40 |
| Heparin | 545 | 20 |
| EDTA | 0 | 0 |
| Trypsin | 150 | 5 |

EXAMPLE 4

M-EDTA and the Prevention of Biofilm Formation

The present example is provided to demonstrate the utility of the M-EDTA preparation in preventing staphylococcal biofilm formation at the surface of a catheter, as well as to demonstrate the anti-staphylococcal activity of the preparation at high staphylococcal concentrations.

The method of Example 3 was used with the following modifications:

1. A more intense exposure to staphylococci (*S. epidermidis* and *S. aureus*) was achieved by flushing the MRD for 6 hours (instead of 3 hours in Example 3) with $3 \times 10^6$ CFU of staphylococci per ml of $D_5/W$; and
2. The growth of adherent staphylococci to the catheter segments was promoted and achieved by exposing the catheter segments at 37° C. to a 10% broth solution (prepared by adding 1 ml of trypticase soy broth to 9 ml of sterile $H_2O$) of EDTA (30 mg/ml of 10% broth), Mino/EDTA (30 mg/3 mg per ml of 10% broth), vancomycin (3 mg/ml of 10% broth), vancomycin/heparin (3 mg vancomycin plus 100 units heparin/ml of 10% broth), or $D_5/10\%$ broth (50 mg/ml of 10% broth solution).

The results from these studies are demonstrated at Table 3 (*S. epidermidis*) and Table 4 (*S. aureus*).

TABLE 3

| Agent Used | No. of adherent *S. epidermidis* colonies obtained from 0.3 cm² catheter surfaces | |
|---|---|---|
| | After 4 hrs. of treatment | After 24 hrs. of treatment |
| Urokinase | $>5 \times 10^3$ | $>5 \times 10^3$ |
| Heparin | $>5 \times 10^3$ | $>5 \times 10^3$ |
| EDTA | 800 | 20 |
| Minocycline | 10 | 0 |
| Minocycline/EDTA | 0 | 0 |
| Vancomycin | 55 | 85 |
| Vancomycin/Heparin | 445 | 40 |
| $D_5/10\%$ broth | $>5 \times 10^3$ | $5 \times 10^3$ |

As demonstrated in Table 3, the urokinase, heparin and dextrose solutions alone were equally ineffective in preventing and eradicating *S. epidermidis* adherence after 4 or 24 hours of catheter treatment. The minocycline and minocycline/EDTA provided effective prevention and eradication of *S. epidermidis* adhesion after only 4 hours of treatment. Minocycline/EDTA was slightly more effective than minocycline alone at 4 hours. EDTA alone and vanco/heparin provided minimal prevention at 4 hours but were more effective after 24 hours. Vancomycin alone provided equal partial prevention at 4 and 24 hours. M-EDTA was superior to all including vancomycin, vancomycin/heparin, minocycline or EDTA alone.

TABLE 4

| Agent Used | No. of adherent *S. aureus* colonies obtained from 0.3 cm² catheter surfaces | |
|---|---|---|
| | After 4 hrs. of treatment | After 24 hrs. of treatment |
| Urokinase | $>5 \times 10^3$ | $5 \times 10^3$ |
| Heparin | 256 | $>5 \times 10^3$ |
| EDTA | 750 | 30 |
| Minocycline | 0 | 0 |
| Minocycline/EDTA | 0 | 0 |
| Vancomycin | 605 | 230 |
| Vancomycin/Heparin | 140 | 185 |
| $D_5/10\%$ broth | $>5 \times 10^3$ | $>5 \times 10^3$ |

All staphylococcus isolates were bloodstream slime-producing isolates obtained from human patient cases with catheter-related bacteremia.

Table 4 demonstrates that minocycline and minocycline/EDTA solutions were the most effective inhibitors of *S. aureus* adhesion, with 0 adherent colonies being observed after 4 hours of treatment. EDTA alone, vancomycin alone and vancomycin/heparin are significantly less effective for preventing adherent *S. aureus*. These later three preparations had some partial anti-adherent activity, particularly after 24 hours of treatment.

These data (Table 3 and Table 4) demonstrate that minocycline alone or in combination with EDTA was effective for inhibiting *S. epidermidis* and *S. aureus* adherence and colonization of a catheter surface.

EXAMPLE 5

M-EDTA and the Inhibition of *C. albicans* Adhesion

The present example is provided to demonstrate the utility of the M-EDTA formulation in the inhibition of other glycocalyx and biofilm-forming microorganisms, such as *C. albicans*.

The M-EDTA flush formulation described in Example 1 was employed in the present example. The method employed was the same as that described at Example 4, with the following modifications. The organism used was a *C. albicans* obtained from the bloodstream of a patient with catheter-related candidemia. The infected infusate consisted of $D_5/W$ with $4 \times 10^2$ CFU of *C. albicans* per ml flushed through the MRD for 6 hours. Results from the study are presented in Table 5.

TABLE 5

| Agent Used | After 4 hrs. of treatment | After 24 hrs. of treatment |
|---|---|---|
| Urokinase | $>5 \times 10^3$ | $>5 \times 10^3$ |
| heparin | $>5 \times 10^3$ | $>5 \times 10^3$ |
| EDTA | 1060 | 155 |
| Minocycline | 190 | 535 |
| Minocycline/EDTA | 0 | 0 |
| $D_5/10\%$ broth | $>5 \times 10^3$ | $>5 \times 10^3$ |
| Vancomycin/heparin | $>5 \times 10^3$ | $>5 \times 10^3$ |
| Vancomycin | 740 | $>5 \times 10^3$ |

This example demonstrates minocycline/EDTA as a unique antistaphylococcal and antifungal agent. Vancomycin (a standard antistaphylococcal agent) when used alone or with heparin failed to have any anti-*C. albicans* activity and was not different from dextrose, urokinase or heparin solutions against *C. albicans*.

EDTA alone had some anti-*C. albicans* activity after 24 hours and minocycline alone had some activity at 4 and probably 24 hours. Both in combination (M-EDTA) were synergistic and had an essentially total inhibitory effect against fungal adherence after 4 and 24 hours. Therefore, M-EDTA is unique in preventing staphylococcal and Candida adherence to catheter surfaces (Staphylococci and Candida contributing to 95% to 100% of the pathogenic microbiology of catheter-related infections).

These results demonstrate that the solutions of a mixture of minocycline and EDTA provide a more effective and rapidly-acting preparation for the prevention of *S. epidermidis*, *S. aureus*, and *C. albicans* adhesion to a catheter surface than any other thrombolytic (urokinase), anticoagulant (heparin, EDTA), or antistaphylococcal preparation (minocycline, vancomycin, vancomycin/heparin).

EXAMPLE 6

*S. epidermidis* Biofilm Formation and Heparin, Urokinase and Dextrinase Treatment The present example is provided to examine the relative *S. epidermidis* biofilm-destroying activity of heparin, urokinase and dextrinase as assessed by scanning electron microscopy of an *S. epidermidis*-colonized catheter surface.

Figure 2:
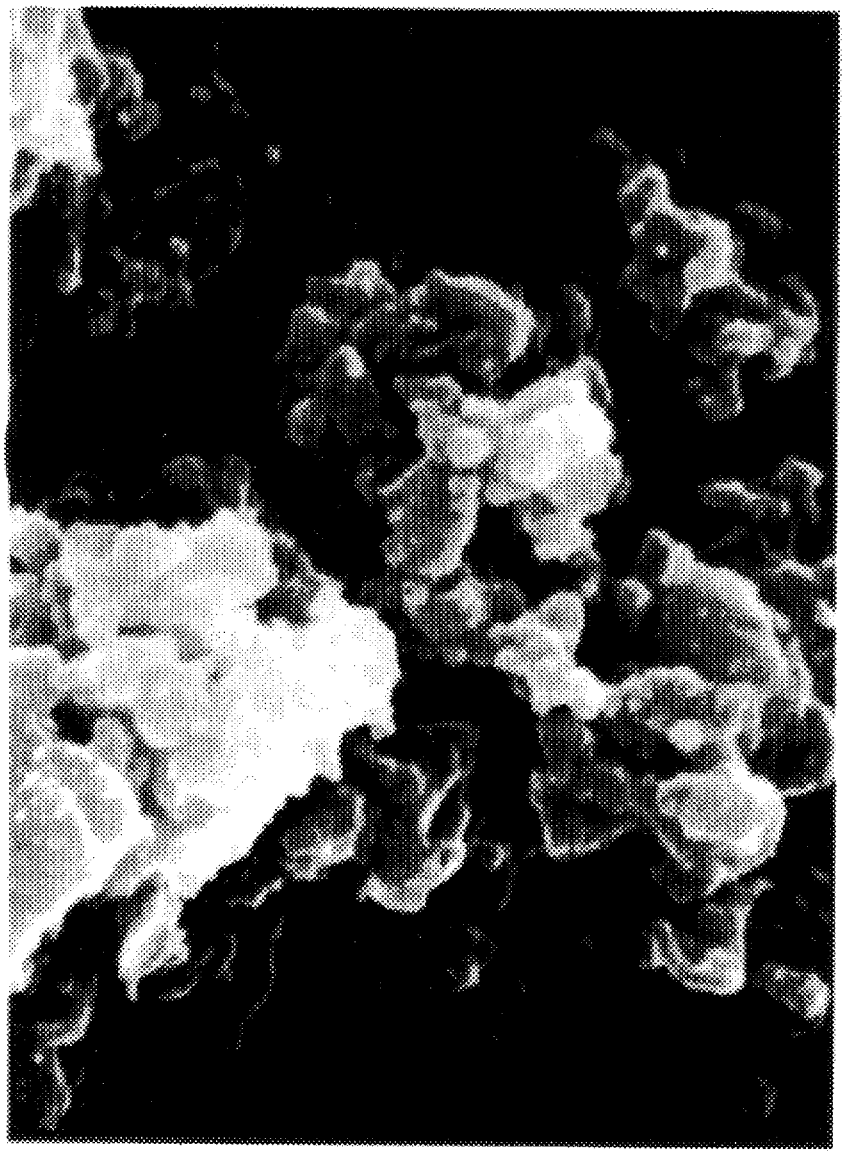
FIG. 2 Scanning electron microscopy picture showing a layer of biofilm from a catheter segment that exposed to slime producing *S. epidermidis* and later immersed in Urokinase for 24 hours. (Example 6 results.)
Figure 3:
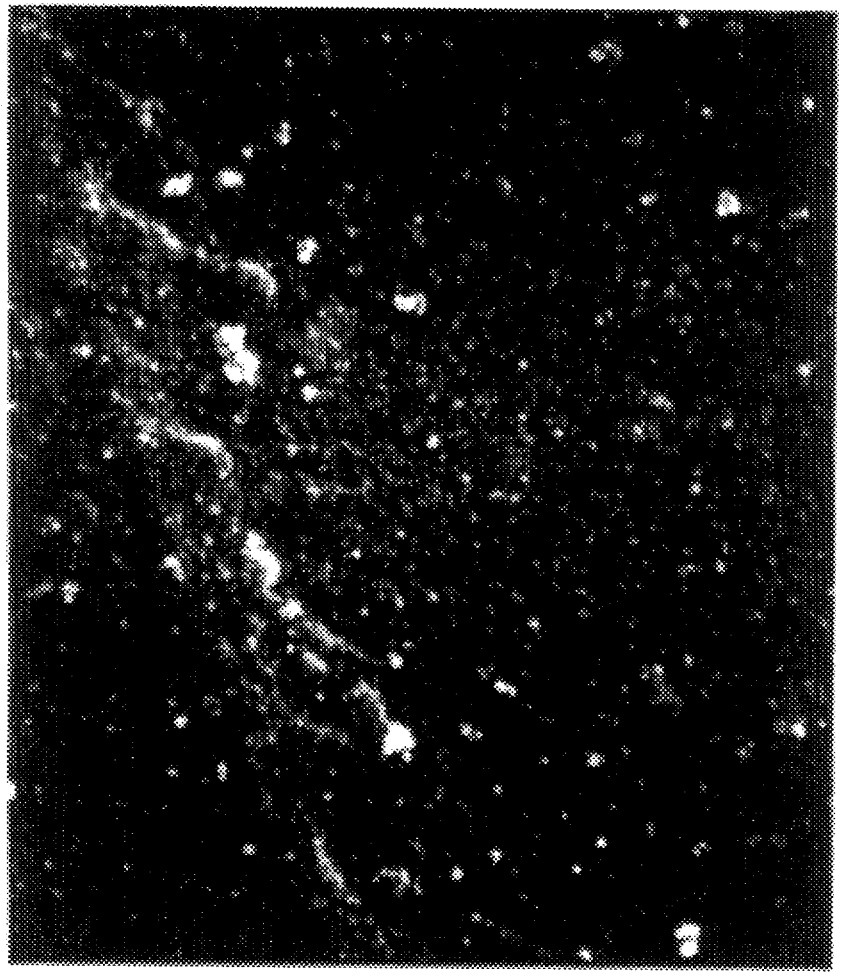
FIG. 3 Scanning electron microscopy picture showing a representative clear surface from a catheter segment exposed to slime producing *S. epidermidis* and later immersed in EDTA for 24 hours. The white particles are dust particles. (Example 6 results.)
Figure 4:
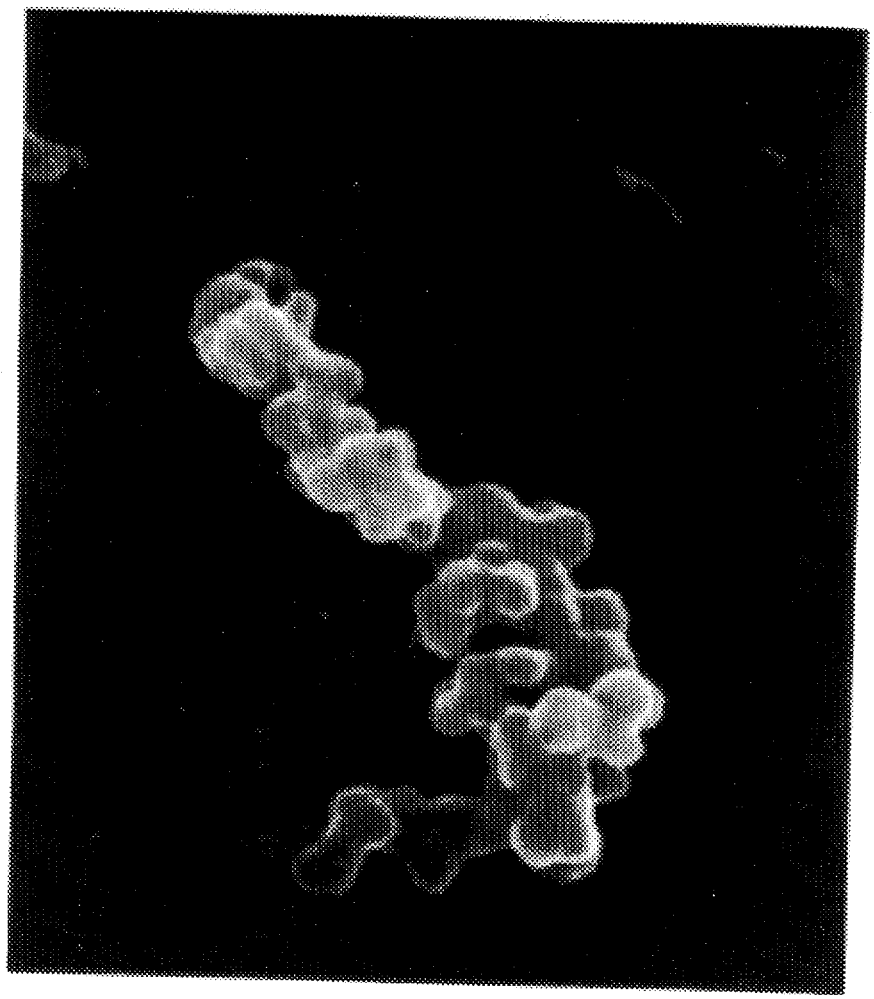
FIG. 4 A scanning electron micrograph at high magnification showing coccal forms in a biofilm layer from a catheter segment coated with control solution (saline) and after exposure to slime producing *S. epidermidis*. (Example 7 results.)

Scanning electron microscopy was done on various segments of a catheter exposed to *S. epidermidis* and then later exposed to heparin, urokinase or dextrinase for 24 hours. A reduction in biofilm (glycocalyx) was noted on colonized catheter surfaces exposed to EDTA for 24 hours, compared to colonized surfaces later exposed to heparin, urokinase, or dextrinase for 24 hours (FIG. 1=Dextrinase; FIG. 2=Urokinase; FIG. 3=EDTA; FIG. 4=Saline).

EXAMPLE 7

Pretreatment of Catheter Surfaces with EDTA Dextrinase or Saline and *S. epidermidis* Biofilm Formation The present example is provided to demonstrate the effect of chemically pretreating a catheter surface with EDTA or dextrinase, compared to a saline control, on biofilm formation and adhesion of *S. epidermidis* to the catheter surface.

Catheter surfaces were coated with EDTA, dextrinase or control (saline), at the concentrations described in Example 5, and then exposed to slime producing *S. epidermidis*.

Figure 5:
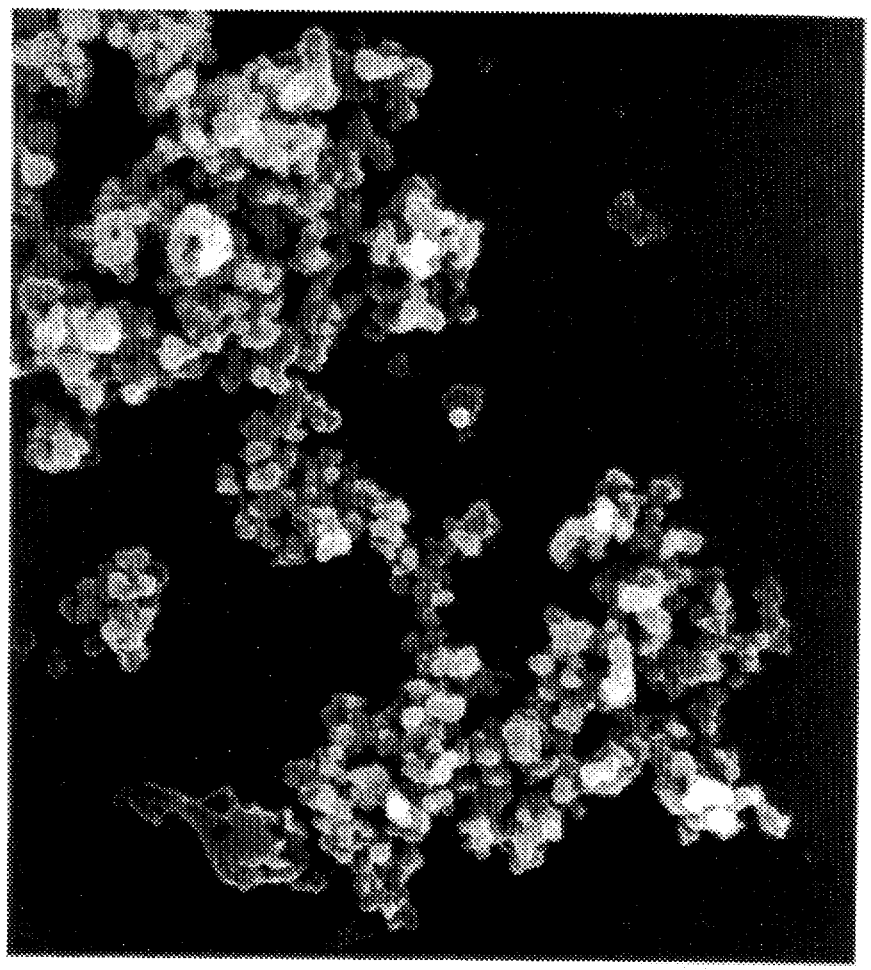
FIG. 5 Lower magnification from a different area of the catheter of FIG. 4 showing coccal forms and biofilm. (Example 7 results.)
Figure 6:
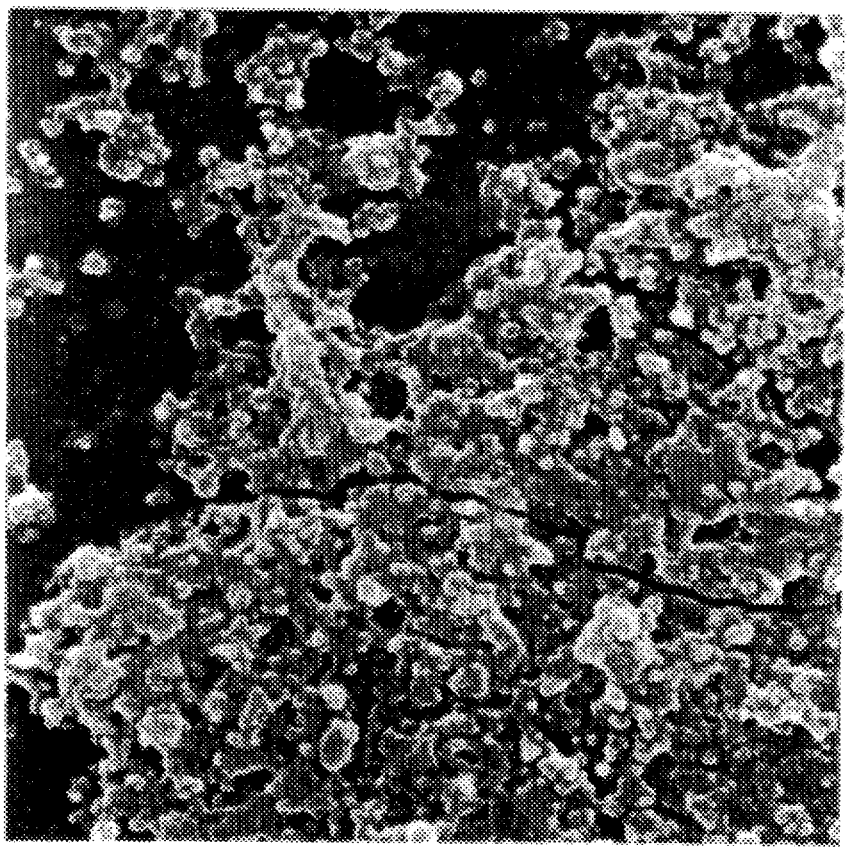
FIG. 6 Dextrinase-pretreated micrograph. A scanning electron micrograph picture showing a catheter surface pretreated or coated with dextrinase, upon exposure to staphylococci. The micrograph shows a thick biofilm layer with many coccal formations. These coccal formations are indicative of staphylococcal colonization.

No biofilm or organisms were observed on EDTA coated surfaces. However, biofilm formation was observed on catheter surfaces pretreated with dextrinase (FIG. 4 and FIG. 5=saline; FIG. 3=EDTA; FIG. 6=Dextrinase pretreated).

EXAMPLE 8

Minocycline Coating of a Catheter and Microbial Colonization

The present example is provided to demonstrate the anti-microbial colonization effect of minocycline at a catheter surface.

Catheter surfaces were coated with minocycline, vancomycin or control cement with $H_2O$, then the inventors exposed catheter surfaces to clinical staphylococci isolates using a Modified Robbin's Device. The Modified Robbin's Device simulates a vascular catheter, and therefore provides a model predictive of in vivo effects with regard to catheters coated according to the herein described studies in humans (see Example 2).

One gram of methylmethacrylate (cement) was mixed with 0.5 ml of sterile $H_2O$ and one of the following:
1. 60 mg of minocycline
2. 60 mg of vancomycin
3. control (cement+$H_2O$ alone)

Equal amounts of cement alone or with minocycline or vancomycin were put in the lumen of catheter latex segments in a specimen plug of the Modified Robbin's Device. Twenty-four hours later, a one-liter infusate bag made of 5% dextrose in water was infected with 5 ml of $10^5$ to $10^8$ colony forming units (CFU) per ml of slime producing *Staphylococcus epidermidis* strains obtained from the bloodstream of patients with catheter related bacteremia. Using a peristaltic pump, the infected infusate was ? segments of the Modified Robbin's Device.

Each catheter segment was made of 30 mm$^2$ silicone with a lumen filled with cement. At the end of 2 hours, some catheter segments (control and antibiotics coated) were taken out from specimen plugs and the cement in the lumen was removed, then the surface that was exposed to the infected fluid was cultured semiquantitatively using the roll-plate technique. Other segments were left behind and flushed with saline solution for 4 hours, then cultured by roll-plate.

Electron microscopy was used to document the adherence of staphylococci and the formation of biofilm layer on the surface of control uncoated catheter segments. Leaching of antibiotics from the cement was demonstrated to occur for a least one week by determining the inhibition around disc-shaped pieces of cement placed on blood agar plates that had been inoculated with bacteria. Coating of the catheter segments with antibiotics was demonstrated by the zone of inhibition that continued to form for at least one week around the disc-shaped catheter segments (without cement) placed on agar plates that had been inoculated with bacteria. The results from this study are presented in Table 6.

TABLE 6

| No. Colonies of *S. Epidermidis* from 30 mm$^2$ Catheter Surface | | |
| --- | --- | --- |
| Coating | Before Flush | After Flush |
| Control | 336 | 128 |
| Vancomycin | 174 | 111 |
| Minocycline | 48 | 15 |

Catheter segments coated with minocycline had a significantly lower number of adherent *Staphylococcus epidermidis* colonies, compared to control and vancomycin coated catheter segments (see Table 6). However, fibrous glycocalyx was not inhibited on the minocycline-coated catheter surfaces. The following scanning electron microscopic figures also evidenced these findings.

Figure 7:
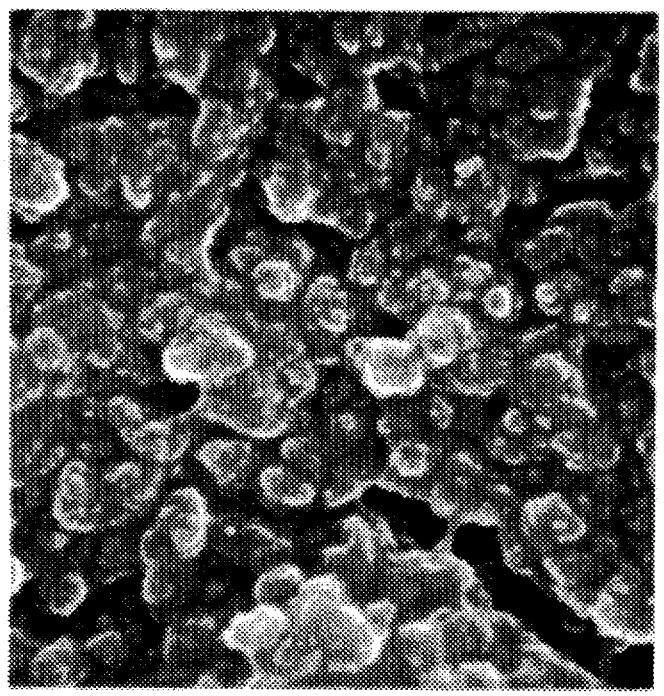
FIG. 7 Electron micrograph demonstrates formation of fibrous glycocalyx on the surface of a control (saline-treated) catheter segment—before flushing with saline for 4 hours.

1. FIG. 7 shows fibrous glycocalyx on the surface of a control catheter segment—before flush.

Figure 8:
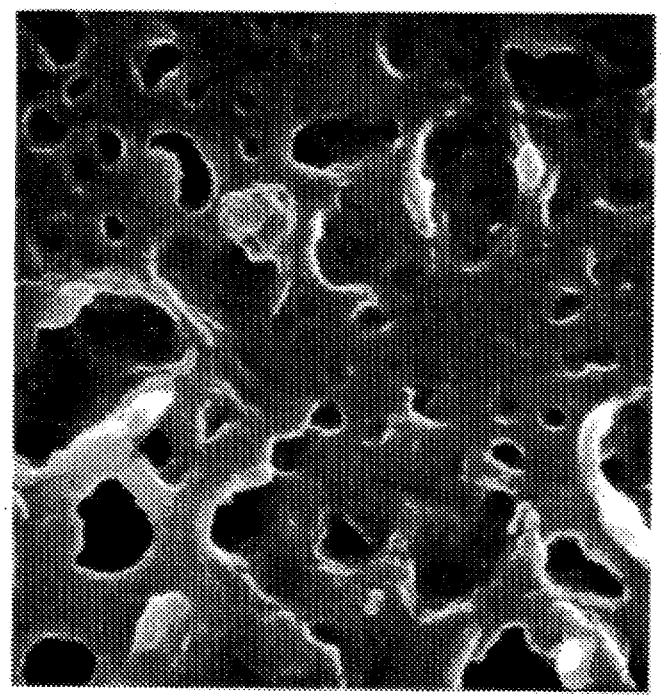
FIG. 8 Electron micrograph demonstrates some deranged fibrous glycocalyx on the surface of a minocycline coated catheter segment—before flushing with saline for 4 hours.

1. FIG. 8 shows some deranged fibrous glycocalyx on the surface of minocycline coated catheter segment—before flush.

Figure 9:
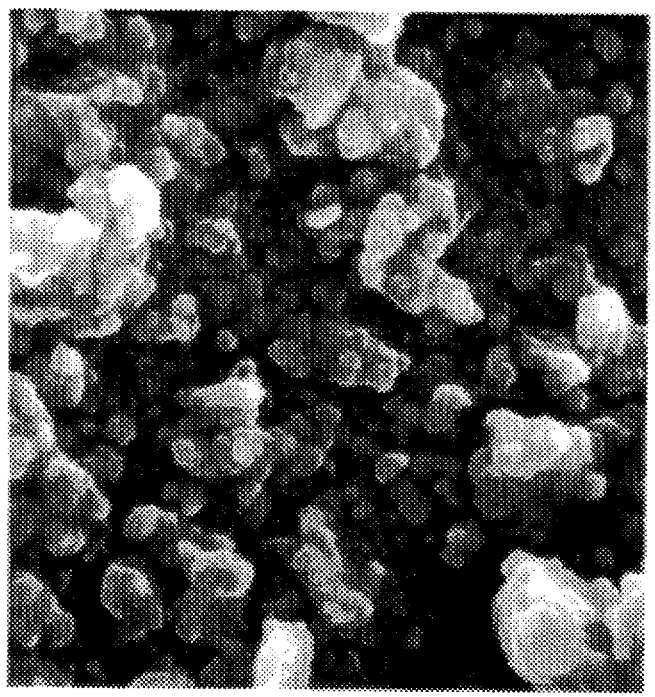
FIG. 9 Electron micrograph demonstrates fibrous glycocalyx on the surface of another control (saline-treated) catheter segment—after flushing with saline for 4 hours.

3. FIG. 9 shows fibrous glycocalyx on the surface of another control (saline) catheter segment after flush.

Figure 10:
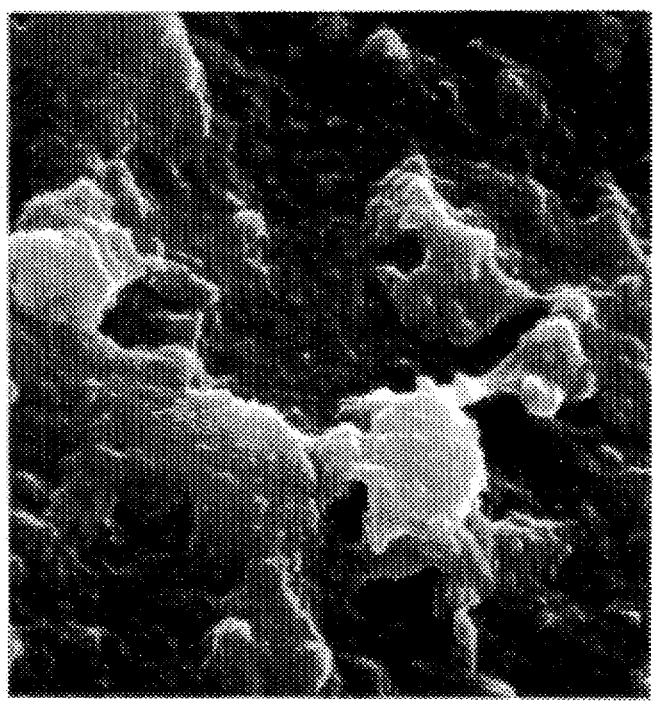
FIG. 10 Electron micrograph demonstrating fibrous glycocalyx on the surface of a minocycline-coated catheter segment—after flushing with saline for 4 hours.

4. FIG. 10 shows fibrous glycocalyx on the surface of minocycline coated catheter segment after flush.

These data demonstrate that the coating of catheters with minocycline alone significantly reduced staphylococcal adherence. Fibrous glycocalyx formation is not inhibited with minocycline coated surfaces.

EXAMPLE 9

Stability of Minocycline and EDTA Pharmaceutical Preparations

The present study will be conducted to characterize the stability of the M-EDTA solutions of the present invention.

The M-EDTA solutions are expected to retain their potency for relatively long periods of time when stored refrigerated at about 4° C., i.e., for at least 1 month.

The solutions of the present invention have also been examined for retained potency at room temperature (37° C.). The M-EDTA solutions have been observed to retain relatively full potency for at least 72 hours at room temperature. It is therefore expected that the formulation has a shelf life that renders it suitable for routine hospital use (Table 1 and FIG. 11).

EXAMPLE 10

Relative Activities of Minocycline and EDTA Preparations

To examine the relative anti-*Candida albicans* activity of mixtures containing different ratios and concentrations of minocycline and EDTA, the following solutions were prepared and tested:

| Solution | Ratio |
| --- | --- |
| (1) 3 mg Minocycline + 30 mg EDTA/ml | 1:10 |
| (2) 2 mg Minocycline + 20 mg EDTA/ml | 1:10 |
| (3) 3 mg Minocycline + 3 mg/EDTA/ml | 1:1 |
| (4) 3 mg/Minocycline + 0.3 mg/EDTA/ml | 10:1 |
| (5) 3 mg/Minocycline + 0.03 mg/EDTA/ml | 100:1 |
| (6) 3 mg/ml Minocycline | — |

The methodology used in this study was described in the U.S. Pat. No. 5,362,754 (Examples 4 and 5, pp. 22–27). The modified Robbins device was used as described at Example 1 of the referenced patent application to determine the relative antimicrobial activity of the various solutions on day 1 of the study, the Robbins device was sterilized and a *Candida albicans* frozen stock was subcultured to a blood agar plate. On day 2, the *Candida albicans* was subcultured to 5 ml of trypticase soy broth, and incubated for 2 hours. A sample of this 5 mls of culture was then diluted 1:100 so as to obtain 30 mls of a 1:100 dilution of the infected broth. This 30 ml was then used to infect 1,000 ml of a normal saline solution. The pump speed was set to run for 24 hours at 40 ml/hr. On day 3, the Robbins device was flushed for 2 hours at a rate of 125 ml/hr. with a saline solution. The plugs of the Robbins device were then removed and the device incubated in one of the following solutions for 24 hours at 37° C.:

| Ratio | |
| --- | --- |
| 1:10 | Minocycline/EDTA |
| 1:1 | Minocycline/EDTA |
| 10:1 | Minocycline/EDTA |
| 100:1 | Minocycline/EDTA |
| 1000:1 | Minocycline/EDTA |
| — | Minocycline |

Culture was by scrape sonicator in 0.5 ml of trypticase soy broth, which was sonicated for 5 minutes.

All cultures were evaluated for adherent *Candida albicans* growth after 24 hours. The following results were obtained:

| | | |
| --- | --- | --- |
| (1) Minocycline/EDTA | 1:10 | 0 |
| (2) Minocycline/EDTA | 1:1 | 0 |
| (3) Minocycline/EDTA | 10:1 | 90 |
| (4) Minocycline/EDTA | 100:1 | >$10^3$ |
| (5) Minocycline/EDTA | 1,000:1 | >$10^3$ |
| (6) Minocycline (3 mg/ml) | | >$10^3$ |

These results demonstrate that solutions with 1% EDTA (100:1 ratio) or less were not as effective for inhibiting *Candida albicans* colonization as were solutions that included at least 10% EDTA (10:1 ratio) together with minocycline. These studies also demonstrate the marked enhancement of anti-*Candida albicans* inhibitory activity where a ratio of minocycline to EDTA of 10:1 (10% EDTA) is used.

EXAMPLE 11

Flush Solution for the Prevention of Catheter Infection

Existing catheter flush solutions, such as heparin flush, are designed to prevent thrombotic occlusion of catheters, not infection. The flush solution used in the present clinical studies possess both antimicrobial and anticoagulant activity. These solutions comprise mixtures of minocycline and EDTA (M-EDTA). EDTA (Edetate disodium is the disodium salt of ethylenediaminetetraacetic acid) is a chelator of divalent and trivalent metals with anticoagulant activity and some antimicrobial activity. Minocycline is a tetracycline antibiotic with broad antistaphylococcal activity. The combination of M-EDTA is shown to have a broad antibacterial antifungal and anticoagulant activity.

Catheter surfaces were exposed to various catheter-related bloodstream isolates that commonly cause catheter sepsis such as *Staphylococcus epidermidis*, *Staphylococcus aureus*, *Candida albicans*, and *Xanthomonas maltophilia*. Equal size (0.3 $cm^2$) silicone segments that were colonized with these adherent organisms were respectively exposed to various anticoagulants and antimicrobial solutions such as urokinase, heparin, vancomycin plus heparin, minocycline and M-EDTA for 4 hours and 24 hours. M-EDTA achieved total sterilization of the infected segments, whereas 20 to 10,000 colonies were isolated from each of the various segments treated with urokinase, heparin, vancomycin plus heparin and EDTA alone.

M-EDTA flush solution was successfully demonstrated in three patients with recurrent catheter infection. All patients had a history of recurrent catheter infections. All three patients had received a prolonged course of intravenous antibiotics.

Patient 1

The first patient is a 41 year old white female with metastatic melanoma who developed in the past a heparin associated thrombocytopenia accompanied by right femoral artery thrombosis which resulted in a right lower extremity ischemia and above knee amputation. Because of the heparin associated complication, this patient had a Groshong silicone central venous catheter flushed every week with saline. Over a period of 5 months of this treatment, this patient developed four recurrent episodes of catheter-related *Enterobacter aerogenes* bacteremia with a relapse frequency every 3–4 weeks despite the use of active intravenous antibiotics. Afterwards, this patient was started on M-EDTA flush solution (3 mg/ml minocycline/30 mg/ml EDTA) every week (once a week), and remained free of catheter infection for 4 months. EDTA was then stopped for a period of 4 weeks. The patient then relapsed with an infection caused by the same infectious organism. The patient was then started on M-EDTA again, and became free of infection for 2 months. The patient died from the underlying disease. Two peak serum samples failed to detect any minocycline or EDTA.

Patient 2

The second patient is a 56 year old male with metastatic melanoma receiving interleukin-2($IL_2$) therapy. During the 6 months of $IL_2$ therapy this patient developed 15 episodes of catheter-associated coagulase negative staphylococcal bacteremia. The patient had nontunneled silastic central venous catheters in the subclavian vein. After this 6 month period of time, the patient was started on M-EDTA (mg/ml minocycline/30 mg/ml EDTA) flush solution and remained free of catheter infections for another 5 months at the end of which the catheter was removed. The semiquantitative rollplate cultures of the tip and subcutaneous segments were negative. Four peak serum samples failed to detect by HPLC any minocycline or EDTA in the blood. Semiquantitative cultures of the tip and subcutaneous segments were negative. The removed catheter inhibited the growth of S. epidermidis on a petri dish plate with a zone of inhibition with a diameter of 12 mm.

Patient 3

The third patient is a 39 year old male with a long history of Crohn's disease over the past 20 years who has a short bowel syndrome resulting in his being maintained on total parenteral nutrition via central access for years. Over the past 4 years this patient has had 22 infected Hickman catheters and venous ports, most of which were caused by S. aureus. Various maneuvers have been tried to decrease the rate of catheter infections, including prolonged course of intravenous antibiotics, ointment to the nares, cleansing of the insertion site with chlorhexidine daily, vancomycin flushes and other maneuvers. A polyurethane catheter having the cationic surfactant tridodecylmethylammonium chloride (TDMAC) which binds antibiotics, was coated with M-EDTA and inserted in the patient via the left internal jugular vein. The catheter was flushed daily with M-EDTA and the patient remained free of infection until the central catheter was removed 10 weeks later. No minocycline or EDTA was detected in serum immediately after flushing. Upon removal, semiquantitative cultures of the tip and subcutaneous segments were negative. Another 2 cm catheter segment inhibited the grown of S. aureus on petri dish plate by creating a zone of inhibition diameter of 22 mm.

EXAMPLE 12

Medical Devices Treated with Minocycline and EDTA Solutions

The present example is provided to demonstrate the use of solutions of a combination of chelating agents, such as EDTA, with tetracycline antibiotics, such as minocycline, to coat the surface of a medical device, particularly a catheter. These techniques may be used with other combinations of chelating agents and tetracycline antibiotics in the same manner as provided with this specific example, such as with EGTA, DTPA, etc.

Bioguard Cook Catheters with TDMACC surfactant were immersed in antibiotic solutions containing the following:

1) 60 mg of Minocycline plus 60 mg of EDTA/ml
2) 60 mg of Minocycline/ml
3) 60 mg of EDTA/ml Catheters were immersed in each of the three solutions listed above for 15 minutes. Bioguard Cook catheters (uncoated by antimicrobials) were used as negative controls. The Arrow gard catheters coated with chlorhexidine and silver sulfadiazine was used as positive control. The Arrow gard catheter is available coated with antimicrobials. This coated catheter has been described by Maki et al. (1977) in a clinical study to decrease the rate of catheter-related bloodstream infection by five-fold.

In the present study, the catheters were divided into three representative sets. The catheter antibiotic activity was determined in vitro by a modified Kirby-Bauer technique. The first set of catheters were tested immediately after immersion without gas sterilization. The second set was tested 24 hours later without gas sterilization. The third set was tested 24 hours after gas sterilization.

The modified Kirby-Bauer technique consisted of growing a strain of slime producing catheter-related bacteremic isolate of Staphylococcus epidermidis for 18 hours in trypticase soy broth then diluting the solution to $10^9$ CFU ml in phosphate-buffered saline. A cotton swab was placed in the staphylococcal suspension and then rubbed across the surface of a trypticase soy agar plate. Individual catheters were cut into 20 mm lengths pressed into agar overlaid with S. epidermidis and incubated overnight at 37° C. Zone sizes were assessed by measuring the diameter perpendicular to the long axis of the catheter. The following data were obtained.

EXAMPLE 13

Efficacy of Antibiotic Coated Catheters After Gas Sterilization

The present example is provided to demonstrate the stability of the coated devices to sterilization processes. In order to test the effect of gas sterilization on catheters coated with Minocycline, EDTA and the combination of drugs, the following studies were performed.

M-EDTA-coated catheters were prepared as described in Example 12. The catheters were then divided into three representative groups. The catheter antibiotic activity was determined in vitro by a modified Kirby-Bauer technique described in Sherertz et al. (1989), which reference is specifically incorporated herein by reference for this purpose. The first set of catheters were tested immediately after immersion without gas sterilization. The second set was tested 24 hours later without gas sterilization. The third set was tested 24 hours after gas sterilization.

The modified Kirby-Bauer technique consisted of growing a strain of slime producing catheter-related bacteremic isolate of Staphylococcus epidermidis for 18 hours in trypticase soy broth, then diluting the solution to 10 CFU ml in phosphate-buffered saline. A cotton swab was placed in the staphylococcal suspension and then rubbed across the surface of a trypticase soy agar plate. Individual catheters were cut into 20 mm lengths pressed into agar overlaid with S. epidermidis and incubated overnight at 37° C. Zone sizes were assessed by measuring the diameter perpendicular to the long axis of the catheter. The data in Table 7 demonstrates that Catheters treated with the M-EDTA preparations maintained the greatest post-sterilization zone of inhibition (0 hours=40; 24 hours=34).

For the in vivo studies, the catheters were cut into 2 cm segments and then emersed in 60 mg/ml EDTA, 60 mg/ml minocycline solution each and then immersed in a solution of a mixture containing 60 mg/ml mino and 60 mg/ml EDTA for 15 minutes. All catheters were allowed to dry for one hour and they were gas sterilized.

Table 7 provides the results achieved with these studies. This data demonstrates the superior anti-*S. epidermidis* activity of the M-EDTA coating as compared to non-treated as well as the Arrow Gard catheters.

TABLE 7

| | S. EPIDERMIDIS ZONE OF INHIBITION - DIAMETER (mm) | | |
|---|---|---|---|
| | Pre Sterilization | | Post Sterilization |
| | 0 Hrs | 24 Hrs | 24 Hrs |
| Minocycline | 36 | 33 | 18 |
| M-EDTA | 40 | 34 | 35 |
| EDTA | 5 | 18 | 10 |
| Control | 0 | 0 | 0 |
| Arrow Gard* | 13 | 15 | 7 |

*Coated with chlorhexidine gluconate and silver sulfadiazine

EXAMPLE 14

Efficacy of Antibiotic Coated Catheters After Gas Sterilization to *S. Aureus*

The present example is provided to further demonstrate the stability of the described M-EDTA coatings to sterilization processes, such as gas sterilization, particularly as measured through the retained anti-microbial activity of the device.

The protocol of Example 13 was used to prepare the catheters used in this study (using a catheter-related bacteremic strain of *S. aureus*). The 0 hour catheters, and catheters coated with minocycline or EDTA alone were not included in the study.

TABLE 8

| | S. AUREUS ZONE OF INHIBITION - DIAMETER (mm) | |
|---|---|---|
| | Pre Sterilization 24 Hrs | Post Sterilization 24 Hrs |
| M-EDTA | 31 | 29 |
| Control | 0 | 0 |
| Arrow Gard* | 13 | 13 |

*Coated with chlorhexidine gluconate and silver sulfadiazine

This data demonstrates that gas sterilization did not affect the antibiotic activity of minocycline-EDTA coated catheters and that these catheters were at least two times more active than the Arrow septic catheters.

EXAMPLE 15

Comparative Efficacy of M-EDTA Coated Catheters Against Catheter Related Micro-Organisms To test the broad spectrum activity of M-EDTA catheters and the in vitro comparative efficacy, the above zone of inhibition experiments were done using M-EDTA coated catheters and Arrow gard catheters against different catheter-related organisms such as *Staphylococcus epidermidis, Staphylococcus aureus, Candida albicans* and gram negative bacilli (*Pseudomonas aeruginosa, Xanthomonas maltophilia*, and *acinetobacter* species). These results are outlined in this Example. It should be noted that a recent review of the literature has shown that approximately 60% of catheter infections are caused by *S. epidermidis*, 10% by *S. aureus*, 10% C. albicans, 20% by gram negative bacilli (mostly *P. aeruginosa, X. Maltophilia*, and *acinetobacter* species.) The aim of these experiments is the show that catheters coated with M-EDTA have a broad spectrum activity against different species of bacteria and fungi as well as different strains of the same species. Sherertz and co-workers have recently shown that zones of inhibitions of antimicrobial catheters correlate with the efficacy of these catheters in vivo and (Sherertz et al., 1993). A zone of inhibition of a $\geq 15$ mm is a predictor of excellent efficacy in veins. A zone of 10–15 mm is a predictor of moderate efficacy and a zone of inhibition of $\leq 10$ mm is a predictor of poor efficacy.

Comparative Efficacy of M-EDTA Coated Catheters Against *Staphylococcus epidermidis* (SE) Strains The data in Table 9 demonstrates that the M-EDTA coated catheters has a significantly greater zone of inhibition to five strains of *staphylococcus epidermidis*, as compared to non-M-EDTA coated catheters (Arrow Gard catheters).

TABLE 9

| | ZONES OF INHIBITION - DIAMETER (mm) | | |
|---|---|---|---|
| Strain No. | Arrow Gard | Mino/EDTA | P Value |
| SE 4392 | 14 | 31 | |
| SE 3996 | 16 | 29 | |
| SE 4345 | 17 | 39 | |
| SE 4023 | 15 | 29 | |
| SE 93 | 15 | 31 | |
| Mean (SD) | 15.4 (±1.1) | 31.8 (±4.15) | 0.001 |

Comparative Efficacy of M-EDTA Coated Catheters Against *Staphylococcus aureus* (SE) Strains Table 10 sets forth data obtained employing five different strains of *Staphylococcus aureus* (SA) in the aforedescribed zone of inhibition assays. The data demonstrate that the M-EDTA coated catheters provided a significantly greater zone of inhibition compared to the non-M-EDTA catheters (Arrow Gard).

TABLE 10

| | ZONES OF INHIBITION - DIAMETER (mm) | | |
|---|---|---|---|
| Strain No. | Arrow Gard | Mino/EDTA | P Value |
| SE 1445 | 13 | 23 | |
| SE 1432 | 15 | 28 | |
| SE 1414 | 12 | 23 | |
| SE 48 | 14 | 23 | |
| SE 1411 | 12 | 34 | |
| Mean (SD) | 13.2 (±1.3) | 26.2 (±4.9) | 0.005 |

Comparative Efficacy of M-EDTA Coated Catheters Against *Candida albicans*

Table 11 sets forth data obtained employing the organism *Candida albicans*, in the zone of inhibition study protocol, comparing the inhibitory action of the M-EDTA and non-M-EDTA coated catheters especially. "Ampho B" stands for a broad spectrum antibiotic. The data in Table 11 demonstrates that the M-EDTA treated catheters had superior anti-*Candida albicans* inhibitory activity as compared to control and the three other catheter types (coatings) tested.

TABLE 11

| | Trial #1 | Trial #2 | Trial #3 |
|---|---|---|---|
| M-EDTA | 16 | 21 | 16 |
| Minocycline | 0 | 0 | 0 |
| Control | 0 | 0 | 0 |
| Arrow Gard | 10 | 9 | 9 |
| Ampho B | ND | 18 | 18 |

Comparative Efficacy of M-EDTA Coated Catheters Against *Candida albicans* (CA) Strains Table 12 sets forth data obtained in studies with five strains of *Candida albicans*, and again demonstrates the broad range anti-microbial activity of the M-EDTA coated catheters.

TABLE 12

| | ZONES OF INHIBITION - DIAMETER (mm) | | |
|---|---|---|---|
| Strain No. | Arrow Gard | Mino/EDTA | P Value |
| CA 291 | 0 | 16 | |
| CA 596 | 10 | 12 | |
| CA 276 | 10 | 10 | |
| CA 267 | 10 | 13 | |
| CA 319 | 7 | 18 | |
| Mean (SD) | 7.4 (±4.3) | 13.8 (±3.2) | 0.030 |

Comparative Efficacy of M-EDTA Coated Catheters Against Acinetobacter (ACIN) Strains Table 13 demonstrates the efficacy of the described M-EDTA coatings for inhibiting acineofactor.

TABLE 13

COMPARATIVE EFFICACY OF M-EDTA COATED CATHETERS AGAINST ACINETOBACTER (ACIN) STRAINS

| | ZONES OF INHIBITION - DIAMETER (mm) | | | |
|---|---|---|---|---|
| Strain No. | M/EDTA | TMP/SMX | CFTZ | ARROW GARD |
| ACIN639 | 30 | 00 | 00 | 00 |
| ACIN38B | 23 | 30 | 15 | 05 |
| ACIN632 | 24 | 10 | 00 | 00 |
| ACIN633 | 10 | 15 | 00 | 09 |
| ACIN1771 | 43 | 14 | 00 | 12 |
| Mean* | 26 | 14 | 3.0 | 5.2 |
| STDEV | 12 | 11 | 6.7 | 5.3 |

M = Minocycline; CFTZ = Ceftazidime; TMP-SMX = Trimethoprim-Sulfamethoxazole
*The efficacy of the catheter coated with M-EDTA was significantly higher than the Arrow gard (P = 0.016)

Comparative Efficacy of M-EDTA Coated Catheters Against *P. aeruginosa* (PSA) Strains Table 14 demonstrates the efficacy of the M-EDTA catheters against *x. maltophilia* strains.

TABLE 14

| | ZONES OF INHIBITION - DIAMETER (mm) | | | |
|---|---|---|---|---|
| Strain No. | M/EDTA | TMP/SMX | CFTZ | ARROW GARD |
| PSA1644 | 15 | 00 | 13 | 03 |
| PSA2455 | 11 | 05 | 20 | 00 |
| PSA2451 | 11 | 00 | 20 | 06 |
| PSA2456 | 14 | 00 | 29 | 00 |
| PSA2452 | 10 | 00 | 28 | 06 |
| Mean* | 12.2 | 1.0 | 22 | 3.0 |
| STDEV | 2.17 | 2.24 | 6.60 | 3.0 |

*The efficacy of the catheter coated with M-EDTA was significantly higher than the Arrow gard (P = 0.009)

Comparative Efficacy of M-EDTA Coated Catheters Against *X. Maltophilia* (XMAL) Strains Table 15 demonstrates the efficacy of the M-EDTA coated catheters against *P. aeruginosa* (PSA) strains.

TABLE 15

| | ZONES OF INHIBITION - DIAMETER (mm) | | | |
|---|---|---|---|---|
| Strain No. | M/EDTA | TMP/SMX | CFTZ | ARROW GARD |
| XMAL5653 | 24 | 37 | 32 | 23 |
| XMAL2496 | 34 | 22 | 29 | 00 |
| XMAL8929 | 37 | 40 | 20 | 00 |
| XMAL2657 | 35 | 30 | 15 | 04 |
| XMAL2172 | 15 | 15 | 20 | 00 |
| Mean* | 29 | 28.8 | 23.3 | 3.0 |
| STDEV | 9.30 | 10.38 | 7.05 | 5.22 |

*The efficacy of the catheter coated with M-EDTA was significantly higher than the Arrow gard (P = 0.0016)

These results demonstrate that M-EDTA coated catheters have a broad spectrum activity against various microbial agents that can cause CVC related infections. This activity is superior and broader than the Arrow gard catheters, recognized as a clinically efficacious in preventing catheter infections.

EXAMPLE 16

Shelf Life and Stability of the M-EDTA (In Serum) Device

The present example demonstrates the shelf life (at 25° C.) and stability of the coated M-EDTA on the catheters (at 37° C. in serum). Catheters coated with M-EDTA as well as control and Arrow catheters were tested at baseline (day 1-D1) against *S. epidermidis* by zones of inhibition. Then the same catheters were placed in serum at 37° C. and tested at days 3, 7, 15 and 30 to determine efficacy with time. In addition, segments of the same catheters were kept for 30 and 60 days at 25° C. then tested to determine shelf life.

TABLE 16

STABILITY OF M-EDTA COATED CATHETERS

| | ZONES OF INHIBITION - DIAMETER (mm) Days After Coating & Incubating in Serum (37° C.) | | | | |
|---|---|---|---|---|---|
| | D1 | D3 | D7 | D15 | D30 |
| M-EDTA | 31 | 21 | 16 | 14 | 10 |
| Control | 0 | 0 | 0 | 0 | 0 |
| Arrow Gard | 14 | 07 | 07 | 05 | 03 |

TABLE 17

STABILITY OF M-EDTA COATED CATHETERS

ZONES OF INHIBITION - DIAMETER (mm)

|  | DAY 30 | | DAY 60 |
|---|---|---|---|
|  | Serum 37° C. | 25° C. | 25° C. |
| M-EDTA | 10 | 34 | 32 |
| Control | 0 | 0 | 0 |
| Arrow Gard | 3 | 13 | 12 |

These studies demonstrate that M-EDTA coated catheters maintain excellent efficacy for at least two weeks in serum at 37° C. and at least two months at 25° C. The efficacy of the Arrow gard catheters decreases rapidly within three days in serum (37° C.).

EXAMPLE 17

In Vivo Efficacy of M-EDTA Coated Catheters

Animal studies with polyurethane catheters coated with minocycline plus EDTA are provided. The results are consistent with the extensive in vitro data described herein, and are representative of expected efficacy in use with other animals, such as humans. The catheters produced by Arrow are coated with chlorhexidine gluconate and silver sulfadiazine. These catheters have been shown by a clinical study done by Maki et al. (1977) to reduce the rate of catheter-related sepsis five fold.

An established rabbit model was used whereby catheters were inserted percutaneously. Immediately after insertion, the catheter insertion site was inoculated with 0.1 ml of $10^5$ colony forming units (CFU) of *Staphylococcus aureus* from the bloodstream of a patient with catheter-related *S. aureus* bacteremia. Seven days after insertion the catheters were removed and the subcutaneous (SQ) as well as the tip of the catheters were cultured by quantitative catheter cultures.

Catheters were first pretreated with a cationic surfactant tridodecylmeylammonium chloride (TDMAC). Other surfactants, such as benzalkonium chloride, may also be used to pretreat the device according to well known techniques recognized by those of skill in the art. Treatment of a catheter with a surfactant will enable subsequent bonding of anionic substances, such as the antibiotic minocycline (mino) and EDTA, to a surface. For the present studies, polyethlylene catheters already coated with TDMAC were immersed in a 60 mg/ml EDTA and 60 mg/ml minocycline solution, (Bio-Guard AB coating, Cook Critical Care, Bloomington, Ind.). These polyethylene catheters were manufactured by Cook Critical Care (Bloomington, Ind.), 5.0 Fr (18 ga), 15 cm (5⅞ in)). For these in vivo studies, the catheters were cut into 6 cm segments before treating with the M-EDTA solution.

Solution A. 3 vials of minocycline (100 mg each) diluted with 0.8 ml of sterile water for injection, USP to obtain 2.4 ml of 120 mg/ml minocycline;

Solution B. 1.6 ml of 150 mg/ml EDTA was added to 0.4 ml sterile water to obtain 2 ml of 120 mg/ml EDTA. Finally, 2 ml of solution A was added to 2 ml solution B, resulting in a 4 ml solution of 60 mg/ml minocycline and 60 mg/ml EDTA.

All catheters used were of the polyurethane type made by Arrow or Cook. The following results were obtain in the experiment where catheters were cultured by either the standard semiquantitative roll-plate culture technique (Maki et al., 1977) or the sonication (Sherertz et al., 1990) technique.

The data in the following tables demonstrated the consistently inhibitory activity of the M-EDTA coated catheters against *S. aureus* colonization.

TABLE 18

EFFICACY OF M-EDTA COATED CATHETERS IN A RABBIT MODEL

NUMBER OF COLONIES CULTURED BY ROLL-PLATE

| Catheter Type | Catheter Tip | Catheter SO* |
|---|---|---|
| Control | >1000 | >1000 |
| Control | >1000 | >1000 |
| Arrow Gard<sup>τ</sup> | 2 | 10 |
| Arrow Gard | 0 | 0 |
| Arrow Gard | ? | 10 |
| Arrow Gard | 2 | 8 |
| M-EDTA | 0 | 0 |
| M-EDTA | 0 | 0 |

<sup>τ</sup>Coated with chlorhexidine gluconate and silver sulfadiazine
*Subcutaneous catheter segment

TABLE 19

EFFICACY OF M-EDTA COATED CATHETERS IN A RABBIT MODEL

NUMBER OF COLONIES CULTURED BY ROLL-PLATE

| Catheter Type | Catheter Tip | Catheter SO* |
|---|---|---|
| Control | >1000 | >1000 |
| Control | 18 | 25 |
| Arrow Gard<sup>τ</sup> | 1000 | >1000 |
| Arrow Gard | 1 | 16 |
| M-EDTA | 0 | 0 |
| M-EDTA | 0 | 0 |

In this study catheter segments were cultured by the quantitative sonication technique. The data in Table 20 was obtained using catheter segments cultured by the quantitative sonication technique (as described by Sheretz et al., 1989). This data demonstrates again the consistently anti-*S. aureus* colonizing effect provided through coating a catheter or other device with a combination of minocycline and EDTA.

TABLE 20

EFFICACY OF M-EDTA COATED CATHETERS IN A RABBIT MODEL

NUMBER OF COLONIES CULTURED BY SONICATION

| Catheter Type | Catheter Tip | Catheter SO* |
|---|---|---|
| Control | 40 | 60 |
| Control | 380 | >1000 |
| Arrow Gard<sup>τ</sup> | 180 | >1000 |
| Arrow Gard | 0 | 20 |
| M-EDTA | 0 | 0 |
| M-EDTA | 0 | 0 |

These studies demonstrate the complete prevention of colonization upon using M-EDTA coated catheters compared to partial prevention (with occasional breakthrough) by the Arrow gard.

EXAMPLE 18

Comparative Clinical Trail of M-EDTA and Heparin for the Prevention of Catheter-Related Infections The present example outlines a study wherein the relative effectiveness of an M-EDTA catheter flushing solution will be compared to a heparin flushing solution (a currently used standard preparation) for the prevention of catheter-related infections and occlusions in humans.

The objective of these studies is to further document the utility of the M-EDTA flush solution as compared to a heparin flush solution in preventing infection and/or occlusion in central venous catheters (CVC).

Inclusion Criteria

1. Patients must have a new ($\leq 7$ days old) functioning central venous catheter, utilized for infusion of chemotherapy, blood products, or other intermittent infusions.
2. Patients must have life expectancy or the planned duration of the study and must have catheter in place for study duration (study duration for a single patient is 6 months).

Exclusion Criteria

1. Patients with an occluded central venous catheter.
2. Patients with any existing local or systemic catheter infection.
3. Patients requiring previous catheter removal due to venous thrombosis.

Treatment plan: Patients will be randomly assigned and in double blind manner to have their CVC flushed with either M-EDTA or Heparin according to the following:

1. Tunneled CVC (Hickman/Broviac) will receive either
   (a) two mls or M-EDTA (consisting of 3 mg of minocycline and 30 mg EDTA/ml) q daily
   (b) two mls of Heparin (100 U/ml q daily)
2. Infusion ports will receive either
   (a) two mls of M-EDTA q 3 weeks
   (b) two mls of Heparin (100 U/ml) q 3 weeks Endpoints and Treatment Evaluation: All patients will be followed up for 6 months and will be evaluated for 2 endpoints: catheter infection/colonization and occlusion. Catheter infection will include local CVC-related infection or systemic catheter-related septicemia. Catheter colonization will include positive quantitative catheter culture (flush technique) or positive quantitative blood culture through the CVC in the absence of a positive peripheral blood culture or clinical manifestations of sepsis (fever, chills or hypotension). Patients in the study who develop fever will be evaluated, and simultaneous quantitative blood cultures through CVC and peripheral vein conducted. Catheter occlusion will be categorized as complete or partial depending on whether one cannot withdraw blood, infuse fluids through the CVC, or both. This subgroup of infected catheters will be analyzed separately.

Statistical Considerations: Based on a surveillance study conducted by the inventors (see Table 21), the rate of CVC-related sepsis in pediatric oncology patients ranges from 15%–20.5% (see Table 20). Assuming a conservative total infection rate of 15% and assuming that M-EDTA will lower this rate to 5%, 140 patients will be required in each arm.

TABLE 21

Infection Rates Associated with Hickman/Broviac Catheters and Implantable Ports in pediatric Oncology patients, per 100 catheters

| Type of Infection | Hickman/Broviac (N) | Port (N) | Total (N) |
|---|---|---|---|
| LOCAL CATHETER INFECTION | 17.9 (7) | 3.0 (3) | 7.2 (10) |
| Exit site or port infection | | | |
| Extraluminal infection (tip $\geq$15 cfu) | 0 (0) | 0 (0) | 0 (0) |
| Infection secondary to intraluminal colonization | 7.7 (3) | 3.0 (3) | 4.3 (6) |
| Tunnel tract infection | 2.6 (1) | N/A | 0.7 (1) |
| Total | 28.2 (11) | 6.0 (6) | 12.2 (17) |
| CATHETER-RELATED SEPSIS | 7.7 (3) | 2.0 (2) | 3.6 (5) |
| Definite | | | |
| Probable & physician diagnosed | 12.8 (5) | 13.0 (13) | 12.9 (18) |
| Total | 20.5 (8) | 15.0 (15) | 16.5 (23) |
| #Catheters | N = 39 | N = 100 | N = 139 |

The results from the proposed study will be employed in the further development of a clinical protocol for the treatment and infection-free maintenance of indwelling catheters in humans.

EXAMPLE 19

Preparation of M-EDTA-Coated Devices for In Vivo Use

The present example is provided to demonstrate the utility of a preparation of an anti-microbial agent and a chelating agent, such as an M-EDTA solution, as a coating material for medical devices, most particularly catheters.

Any of a variety of coating techniques may be used for imparting a protective covering of the M-EDTA solution, or other combination of chelating agent and non-blycopeptide antibiotic to a device.

Coating Methods for Medical Devices

As noted, preparations of the present invention may be advantageously used as a coating preparation for treating the surfaces of a medical device. The medical devices which are amendable to coatings with the subject preparations of the invention generally have surfaces composed of thermoplastic or polymeric materials such as polyethylene, Dacron, nylon, polyesters, polytetrafluoroethylene, polyurethane, latex, silicone elastomers and the like. Devices with metallic surfaces are also amenable to coatings with the disclosed combinations. Such devices, for example indwelling catheters of types listed herein, can be coated by cement mixture containing the subject antimicrobial/chelating competitions. Particular devices especially suited for application of the preparation include intravascular, peritoneal, pleural and urological catheters, heart valves; cardiac pacemakers; vascular shunts; and orthopedic, intraocular, or penile prosthesis.

Various methods can be employed to coat the surfaces of medical devices with the described preparations. One of the simplest methods would be to flush the surfaces of the device with the preparation. Generally, coating the surfaces by a simple flushing technique would require convenient access to the implantable device. For example, catheters, are generally amenable to flushing with a solution of the various preparations provided herein. For use in flushing solutions, the effective concentration of the non-glycopeptide antimicrobial agent would range from about 0.001 to about 1000 mg/ml (preferably about 0.001 to about 100 mg/ml, or about 3 mg/ml); and about 0.001 to about 1000 mg/ml of the chelating agent, anticoagulant or antithrombotic agent (preferably between about 1 to about 100 mg/ml or about 30 mg/ml). The flushing solution would normally be further composed of a sterile water or a sterile normal saline solution, or Ringers solution. An example of such a solution would include minocycline as an antimicrobial agent and EDTA or EGTA as the chelating agent.

Another method of coating the devices would be to first apply or adsorb to the surface of the medical device a layer of tridodecylmethyl ammonium chloride (TDMAC) surfactant followed by a coating layer of the solution of non-glycopeptide antimicrobial agent and chelating agent, anticoagulant or antithrombotic agent preparation. Alternatively, the device may be coated with a particular chelating agent alone, anticoagulant, or antithrombotic agent, alone (heparin, hirudin). For example, silastic elastomers, polytetrafluorethylene or Darcon, can be soaked in a 5% by weight solution of TDMAC for 30 minutes at room temperature, air dried, and rinsed in water to remove excess TDMAC. Alternatively, TDMAC precoated catheters are commercially available; for example, arterial catheters coated with TDMAC are available from Cook Critical Care, Bloomington, In. The device carrying the adsorbed TDMAC surfactant coated can then be incubated in a solution of the selected combination for one hour or so, washed in sterile water to remove unbound component ingredients of the solution and stored in a sterile package until ready for implantation. In general, the solution includes between about 0.01 mg/ml to about 1000 mg/ml (or about 100 mg/ml) of the non-glycopeptide antimicrobial agent (preferably 3 mg/ml) in an aqueous pH 7.4–7.6 buffered solution or sterile water. In one embodiment the non-glycopeptide antimicrobial agent is minocycline, and the chelating agent is EDTA, EGTA or DTPA.

Alternative processes and reagents for bonding an agent contained in a solution to a surfactant-coated implantable medical device are provided in U.S. Pat. Nos. 4,442,133, 4,678,660 and 4,749,585, the entire contents of which are incorporated herein by reference for this purpose. A further method useful to coat the surface of medical devices with the subject antibiotic combinations involves first coating the selected surfaces with benzalkonium chloride followed by ionic bonding of the M-EDTA. See, e.g., Solomon et al. (1987) and U.S. Pat. No. 4,442,133.

Other methods of coating surfaces of medical devices with antibiotics are taught in U.S. Pat. No. 4,895,566 (a medical device substrate carrying a negatively charged group having a pKa of less that 5 and a cationic antibiotic bound to the negatively charged group); U.S. Pat. No. 4,917,686 (antibiotics are dissolved in a swelling agent which is adsorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders).

These and many other methods of coating the herein-described preparations to medical devices appear in numerous patents and medical journal articles. As is evident, one of ordinary skill having benefit of this disclosure would be apprised of several different methods of coating various medical device surfaces with the subject inventive minocycline and EDTA coatings.

Medical devices, particularly catheters of the type listed in Table 22, may be coated with the combination solution of a non-glycopeptide antimicrobial agent and a chelating agent, antithrombotic agent or anticoagulant and then stored in a sterile packaging material until use.

TABLE 22

| SHORT-TERM TEMPORARY ACCESS CATHETER | LONG-TERM INDEFINITE VASCULAR ACCESS |
|---|---|
| Peripheral intravenous cannulas | Peripherally inserted central |
| winged steel needles peripheral intravenous catheters | venous catheters (PICC) |
| Arterial catheters | Percutaneous nontunneled silicone catheters |
| Central venous catheters | Cuffed tunneled central venous catheters (Hickman and Broviac) |
| Swan-Ganz catheters | Subcutaneous central venous ports (Infusaport, Port-a-cath, Landmark) |
| Hemodialysis catheters umbilical catheters | |

One particular method whereby the coated medical devices, particularly the catheter device, was coated was as follows:

Bioguard Cook Catheters with TDMACC surfactant were immersed in antibiotic solutions containing the following:
1. 60 mg of Minocycline plus 60 mg of EDTA/ml
2. 60 mg of Minocycline/ml
3. 60 mg of EDTA/ml Catheters were immersed in each of the three solutions listed above for about 15 minutes. Bioguard Cook catheters not treated with any of the 3 solutions listed above (which are not coated by antimicrobials) were used as negative controls. Arrow Gard catheters coated with chlorhexidine and silver sulfadiazine were used as positive control devices. The Arrow Gard catheter is coated with antimicrobials. This catheter is described by Maki et al. (1977) in a clinical study, and reportedly decreased the rate of catheter-related bloodstream infection by five-fold as compared to a standard polyurethane triple-lumen CVC without a chlorhexidine and silver sulfadiazine coating.

EXAMPLE 20

Method for Maintaining Catheter Patency with Minocycline-EDTA Pharmaceutical Preparation The present example demonstrates one proposed embodiment of a method that may be used in maintaining the patency of an indwelling catheter in a patient. The regimen described herein is potentially applicable for use in both pediatric and adult patients. While the particular composition used was minocycline and EDTA the present example is applicable when using any of the comginations of a non-gly-copeptide antimicrobial agent and chelatingagent, anticoagulant or antithrombotic agent.

The particular dose of M-EDTA in the regimen described in this example exposes patients only to relatively low, pharmaceutically acceptable levels of the EDTA and minocycline while providing effective infection control and catheter patency.

An indwelling catheter of a patient will be flushed with a solution of minocycline/EDTA. the "flushing" of the catheter will constitute filling the catheter with a volume of the M-EDTA solution sufficient to provide a concentration of about 9.0 mg minocycline and a concentration of about 90 mg EDTA in the catheter. Assuming a catheter volume of about 2–3 ml., the solution will contain a concentration of EDTA of between about 10 mg/ml–30 mg/ml. "Flushing" the catheter with about 3 ml of the M-EDTA solution will thereby provide a dose of between 3–9 mg minocycline and about 30–90 mg EDTA. The solution of M-EDTA will be prepared as outlined in Example 1.

The "flushing" of the catheter is achieved by adding between 2–3 ml of the M-EDTA solution to the catheter. The solution is then allowed to diffuse throughout the catheter to the patient in which it is implanted. The concentration of the EDTA and minocycline in the solution is such that the patient will be exposed only to concentrations of the agents well below pharmacologically tolerable levels.

The flushing of the catheter is to be repeated at periodic intervals of once a week, once every 4 days, once every 2 days, once a day, twice a day, every four hours or as needed according to patient needs, to assure that infectious organisms are not allowed an opportunity to colonize the surface or initiate biofilm formation on the catheter surface.

EXAMPLE 21

In Vivo Efficacy of M-EDTA Catheters

The present example further demonstrates the anti-microbial activity of the coated M-EDTA devices in vivo. The M-EDTA-coated catheters were prepared as described in Example 17. $10_4$ colony forming units of *S. aureus* were inoculated at the insertion site of a catheter coated with M-EDTA with chlorhexidine gluconate and silver sulfadiazine (the Arrow Gard catheter) or with TDMAC alone with no added antibiotic.

The rabbit model described herein was used in the present study, i.e., New Zealand white rabbits between 2–3 months old and weighing 2–3 kg. The data in Table 23 demonstrates the superior anti-staphylococcal and total inhibitory activity of M-EDTA as compared to the partial anti-*S. aureus* activity achieved with the Arrow Gard catheter.

TABLE 23

NUMBER OF *S. AUREUS* COLONIES CULTURED BY ROLL-PLATE

| Catheter No. | Catheter Type | Catheter Tip | Catheter SQ | Catheter Site Purulence |
|---|---|---|---|---|
| 1 | Control | >1000 | >1000 | Yes |
| 2 | Control | >1000 | >1000 | Yes |
| 3 | Control | >1000 | >1000 | Yes |
| 4 | Control | >1000 | >1000 | Yes |
| 5 | Arrow Gard | 3 | 10 | No |
| 6 | Arrow Gard | 15 | 10 | No |
| 7 | Arrow Gard | 15 | 15 | No |
| 8 | Arrow Gard | 20 | 15 | No |
| 9 | M-EDTA | 0 | 0 | No |
| 10 | M-EDTA | 0 | 0 | No |
| 11 | M-EDTA | 0 | 0 | No |
| 12 | M-EDTA | 0 | 0 | No |
| 13 | M-EDTA | 0 | 0 | No |
| 14 | M-EDTA | 0 | 0 | No |
| 15 | M-EDTA | 0 | 0 | No |
| 16 | M-EDTA | 0 | 0 | No |

EXAMPLE 22

In Vivo Comparative Study of M-EDTA-Coated Catheters V. Chlorhexidine/Silver Sulfadiazine-Coated Catheters For this example, catheters were cultured by a sonication quantitative culture technique described in Sheretz et al. (1990). The Sheretz et al. (1990) article is specifically incorporated herein by reference for this purpose. The sonication of technique is a quantitative culture technique, and is described in Raad et al. (1992). The M-EDTA catheters were coated as described herein. The chlorhexidine/silver sulfadiazine coated catheters are commercially available from Arrow International, Inc. (300 Bernville Road, Reading, Pa. 19605) (Arrow Gold catheters). The data in Table 24 again demonstrates the consistently effective anti-microbial, particularly the anti-*S. aureus*, activity of the M-EDTA coated devices of the invention. As well as the superior anti-microbial activity of the M-EDTA devices as compared to the Arrow Gard catheter.

TABLE 24

NUMBER OF *S. AUREUS* COLONIES CULTURED BY SONICATION

| Catheter Type | Catheter Tip | Catheter SO |
|---|---|---|
| Control | 600 | 520 |
| Control | 400 | 480 |
| Control | 600 | N/A |
| Control | 640 | N/A |
| Arrow Gard | 40 | 80 |
| Arrow Gard | 120 | 80 |
| Arrow Gard | 0 | 160 |
| Arrow Gard | 80 | 160 |
| M-EDTA | 0 | 0 |
| M-EDTA | 0 | 0 |
| M-EDTA | 0 | 0 |
| M-EDTA | 0 | 0 |
| M-EDTA | 0 | 0 |
| M-EDTA | 0 | 0 |
| M-EDTA | 0 | 0 |
| M-EDTA | 0 | 0 |

EXAMPLE 23

In Vivo Anti-Microbial Activity of M-EDTA Catheters

This study was performed in the rabbit model. $10_4$ colony forming units (CFU) of *S. aureus* (a PI strain) were used to infect the catheter insertion site. The catheters were cultured by sonication. (Sheretz et al., 1990). The Arrow Gard and Cook catheters coated with EDTA (Example 17) were employed in the study. The control catheters used were again the Cook catheters that have a coating of TIDMAC, but are without antibiotic or EDTA. Table 25 provides the date collected in this study. The results in Table 25 again demonstrate the in vivo effectiveness of the M-EDTA coated catheters for inhibiting infection by *S. aureus* in vivo.

Catheters were inserted into the subcutaneous space of New Zealand white rabbits 2–3 months old and weighing 2–3 kg. A 0.1 ml of 10 colonies of a virulent *S. aureus* strain (PI strain) was injected at the insertion site. The rabbits were sacrificed on day 7. Catheters were aseptically removed and the 2 cm tip cultured by the sonication technique. The results are shown in Table 25. These results again demonstrate the in vivo effectiveness of M-EDTA against *S. aureus* infection. These results confirm previous experiments whereby M-EDTA coated catheters prevented staphylococcal colonization and catheter infection compared to partial prevention by the Arrow catheters.

TABLE 25

NUMBER OF S. AUREUS COLONIES CULTURED BY SONICATION

| Catheter No. | Catheter Type | Catheter Tip | Catheter Site Purulence |
|---|---|---|---|
| 1 | Control | $>10^5$ | Yes |
| 2 | Control | $>10^5$ | Yes |
| 3 | Control | $>10^5$ | Yes |
| 4 | Control | $>10^5$ | Yes |
| 5 | Arrow Gard | $>10^3$ | No |
| 6 | Arrow Gard | 16 | No |
| 7 | Arrow Gard | 0 | No |
| 8 | Arrow Gard | 0 | No |
| 9 | Arrow Gard | 0 | No |
| 10 | Arrow Gard | 0 | No |
| 11 | Arrow Gard | 0 | No |
| 12 | Arrow Gard | 0 | No |
| 13 | Arrow Gard | 0 | No |
| 14 | M-EDTA | 0 | No |
| 15 | M-EDTA | 0 | No |
| 16 | M-EDTA | 0 | No |
| 17 | M-EDTA | 0 | No |
| 18 | M-EDTA | 0 | No |
| 19 | M-EDTA | 0 | No |
| 20 | M-EDTA | 0 | No |
| 21 | M-EDTA | 0 | No |
| 22 | M-EDTA | 0 | No |

EXAMPLE 24

Packaging and Kits

The present example is provided to describe various packaging techniques that may be employed in providing the described combination preparations as part of a commercially available kit. The kit will optionally include an instruction sheet insert to identify how the kit is to be used.

The combination of the present example is minocycline and EDTA. However, any of the combination of compounds described in the present disclosure may be packaged in a similar manner.

The packaging options below maintain the ingredients, the antibiotic, such as minocycline, and the chelating agent (or anticoagulant, such as EDTA, in an uncombined form. These components are to be combined shortly before use. These packaging options are contemplated to be part of a 2-compartment or three-compartment syringe system to provide a total volume of about 3 ml of the ready to use preparation.

Option 1

Dry Components—3-compartment system

3–9 mg minocycline (dry)—1 compartment

10–100 mg EDTA (powdered)—1 compartment 3 ml diluent (saline or distilled water)—1 compartment When ready for use, the dry components, minocycline and EDTA, will be allowed to mix with the diluent. Final concentration of the mixture should be about 3 mg/ml minocycline and 30 mg/ml EDTA.

Option 2

Dry (a wet/wet® dual chamber syringe, available from Becton-Dickenson, may be used in these applications) EDTA/Minocycline in diluent—2 compartment system.

3–9 mg/ml minocycline

10–100 mg EDTA

When ready for use, the dry EDTA power will be allowed to combined with the minocycline in solution. The minocycline may be suspended in either saline, distilled water, or other physiologically acceptable diluent. Alternatively, the minocycline may be in dry, powered form and the EDTA in solution.

Option 3

EDTA solution/minocycline solution—2 compartment system (a wet/wet® dual chamber syringe, available from Becton-Dickinson, may be used in these applications.)

3–9 mg/ml minocycline

10–100 mg/ml EDTA

When ready for use, the EDTA solution will be combined with EDTA solution. Once combined, the solution will have a concentration of 3 mg/ml minocycline and 30 mg/ml EDTA.

A compartmentalized syringe that may be used to package the compositions of the present invention is available from Bectin Dickenson.

Option 4

Powdered minocycline/EDTA in diluent—2 compartment system. (A liquid/dry® dual chamber syringe, available from Becton-Dickenson, may be used.)

3–9 mg minocycline

10–100 mg/ml EDTA (in a volume of 3 ml of diluent (saline or water))

When ready for use, the dry minocycline powder will be allowed to combine with the EDTA solution. The EDTA can be suspended in either saline or distilled water, or other physiologically acceptable diluent.

Option 5

Dry powdered EDTA/minocycline solution—2 compartment system. (A liquid/dry®dual chamber syringe, available from Becton-Dickenson, may be used.)

3–9 mg minocycline and 10–100 mg EDTA (powdered) 1 compartment 3 ml diluent (saline or distilled water)

When ready for use the dry powder mixture will be allowed to mix with the diluent. Final concentration of the mixture should be about 3 mg/ml minocycline and 30 mg/ml EDTA.

The present various above compartmentalized embodiments of the invention may also be provided in kit form. Such kits would include a container means comprising a volume of diluent, such as saline or sterile water, a second container means comprising a non-glycopeptide antibiotic, such as minocycline or doxycycline, and a third container means comprising a chelating agent, hirudin or heparin. The dry components may optionally be mixed in one compartment. The addition of the diluent would then be performed immediately prior to use.

EXAMPLE 25

Chelating Agent, Antithrombotic Agent or Anticoabulant Combinations with Antimicrobal Agents The present example provides a representative list of specific combinations of ingredients anticipated for use in the practice of the present invention as a flushing solution, medical device (particularly catheter) coating, or pharmaceutical preparation. The term antimicrobial agent as used in the description of the present invention includes non-glycopeptide antibiotics and antifungal agents. A representative list of these antimicrobial agents, particularly defined as non-glycopeptide antimicrobial agents, is provided in the general textbook reference of Sanford Guide to Antimicrobial Theraphy (1994) J. P. Sanford et al., authors (pp. 118, Table 28)), which reference is specifically incorporated herein by reference for this purpose.

A representative list of antibiotics, anti-thrombotic drugs, and particular thrombolytic enzymes, anticoagulants, chelators, and complexing agents that may be used in the preparation of the various embodiments of the invention include:

ANTIBIOTICS aminoglycoside
amphotericin
ampicillin
carbenicillin
cefazolin
cephalosporin
chloramphenicol
clindamycin
erythromycin
gentamicin
griseofulvin
kanamycin
methicillin
nafcillin
novobiocia
penicillin
polymyxin
rifampin
streptomycin
sulfamethoxazole
sulfonamide
tetracycline
trimethoprim
vancomycin

ANTI-THROMBOTIC DRUGS INCLUDING acetylsalicylic acid
dipyridamole
heparin
ibuprofen
indomethacin
prostaglandins
sulfinpyrazone
warfarin

THROMBOLYTIC ENZYMES streptokinase
urokinase
plasminogen activator

ANTICOAGULANTS

HEPARIN
LOW MOLECULAR WEIGHT HEPARIN
ENOXAPARIN SODIUM
COUMARIN & INDANEDIONE DERIVATIVE, ANISINDIONE
WARFARIN
PROTAMINE SULFATE
STREPTOKINASE
UROKINASE
ANTI-THROMBIN III
ATLEPHASE RECOMBINANT, ANISTREPLASE

CHELATORS

DEFEROXAMINE
DIMERCAPROL
EDETATE CALCIUM DISODIUM
EDTA
EGTA
DTPA
DMSA
PENICILLAMINE
SUCCIMER

COMPLEXING AGENTS

AMMONIUM-1-PYRROLIDINE DITHIOCARBANATE
BATHOPHEN ANTHROLINE

Specific combinations contemplated by the inventors include:

EDTA+minocycline
EDTA+minocycline+rifampin
EGTA+non-glycopeptide antibiotics (eg. tetracycline antibiotic+minocycline, doxycycline, oxytetracycline)

Triethylene tetraminedihydrochloride (TTH)+tetracycline antibiotic (minocycline, doxycycline, oxytetracycline)

Hirudin+tetracycline antibiotic (minocycline, doxycycline, oxytetracycline)

Diethylene triamine pentaacetic acid (DTPA)+tetracycline antibiotic (minocycline, doxycycline, oxytetracycline)

Diethylenetriamineacetic acid+tetracycline antibiotic (minocycline, doxycycline, oxytetracycline)

Triethylene tetramine dihydrochloride+tetracycline antibiotic (minocycline, doxycycline, oxytetracycline)

Etidronate® (disodium dihydrogen (1-hydroxyethylidene) bis[phosphonate])+tetracycline antibiotic (minocycline, doxycycline, oxytetracycline)

Heparin+tetracycline antibiotic (minocycline, doxycycline, oxytetracycline).

Dimercaprol+tetracycline antibiotic (minocycline, doxycycline, oxytetracycline).

Citrate+tetracycline antibiotic (minocycline, doxycycline, oxytetracycline).

Methenamine+tetracycline antibiotic (minocycline, doxycycline, oxytetracycline).

EDTA is available as calcium sodium EDTA and sodium EDTA formulations. The most preferred form employed by the present inventors is sodium EDTA. These formulations are provided at a concentration of 150 mg/ml.

As will be appreciated by those of skill in the art, the present list is only intended to be exemplary. Other chelating agents are also expected to be useful in combination with an non-glycopeptide antibiotic or other antimicrobial substance with equal efficacy. In addition, rifampin or any of the rifamycin family of antibiotics, may also be used in the practice of the present invention. These combinations formulated as a coating will preferably further include a material that will enhance adherence or film forming characteristics, of the preparation. As a solution for flushing or other medicinal use, the ingredients will be suspended in a carrier solution such as sterile saline, phosphate buffered saline, dextrose in water, Ringers solution, distilled water or any other physiologically acceptable solution.

REFERENCES

The following references are specifically incorporated herein by reference for the purposes indicated:

Clumeck et al., "Treatment of severe staphylococcal infections with a rifampin-minocycline association," *J. Antimicrob. Chemother.*, 13(S):17–22, 1984.

Condamine et al., *British J. of Haemotology*, 83(1):166–168, 1993.

Evans & Holmes, "Effect of Vancomycin Hydrochloride on *Staphylococcus epidermidis* Biofilm Associated with Silicone Elastomer," *Antimicrobial Agents and Chemotherapy*, 31:889–894, 1987.

Goodman & Gilman, *The Pharmacological Basis of Therapeutics*, 8th edition, Pergamon Press, 1990.

Gu & Neu, *Antimicrobial Agents & Chemotherapy*, 33(11):1998–2003, 1989.

Harper & Epis, "Effect of chlorhexidine/EDTA/Tris against bacterial isolates from clinical specimens," *Microbios.*, 51:107–112, 1987.

Khoury & Costerton, "Bacterial biofilms in nature and disease," *Dialogues in Pediatric Urology*, 14:1–8, 1991.

Machnicka et al., *Folia Histochem. Cytobiol.*, 24(10):65–70, 1986.

Maki et al., *N. Engl. J. Med.*, 296:1305–1309, 1977.

*Merck Index, The,* 11th edition, Merck & Co., Inc. Publishers, 1621, 1989.

Miyake et al., "Effects of ethylenediaminetetraacetic acid and gentamicin on the antibacterial activity of pyridine carboxylic acid derivatives against gram-negative bacilli," *J. Antimicrobial Chemotherapy*, 17(3):327–32, 1986.

Morita et al., *Developmental Pharmacology & Therapeutics*, 19(1):6–9, 1992.

Raad et al., *Diagn. Microbiol. Infect. Dis.*, 15:13–20, 1992.

Nickel et al., "Tobramycin Resistance of *Pseudomonas aeruginosa* Cells Growing as a Biofilm on Urinary Catheter Material.," *Antimicrobial Agents and Chemotherapy*, 27:619–624, 1985.

Root et al., "Inhibitory effect of disodium EDTA upon the growth of *Staphylococcus epidermidis* in vitro: Relation to infection prophylaxis of Hickman catheters," *Antimicrob. Agents Chemother.*, 32:1627–1631, 1988.

Rudy et al., *Medycyna Doswiadcszlnai Mikrobiologia*, 43(304):127–134, 1991.

Said et al., "Expression of HI outer-membrane protein of *Pseudomonas aeruginosa* in relation to sensitivity to EDTA and polymyxin B," *J. Med. Microbial.*, 24:267–274, 1987.

Segreti et al. "In vitro activity of minocycline and rifampin against staphylococci," *Diagn. Microbial. Infect. Dis.*, 12:253–255, 1989.

Sanford Antimicrobial Theraphy (1994) J. P. Sanford, et al., authors, pp. 118, Table 28.

Sheretz et al., *Antimicrob. Agents Chemother.*, 33:114–118, 1989.

Sherertz et al., *J. Clin. Microbiol.*, 28:76–82, 1990.

Sherertz et al., *Journal of Infectious Diseases*, 167:98–106, 1993.

Solomon et al., *J. Controlled Release*, 6:343–352, 1987.

Tojo et al., "Isolation and characterization of a capsular polysaccharide adhesion from *Staphylococcus epidermidis*," *J. Infect. Dis.*, 157:713–722, 1988.

Winstanley et al., *J. Antimicrobial Chemotherapy*, 25(4):551–560, 1990.

Yourassowsky et al., "Combination of minocycline and rifampin against methicillin and gentamicin resistant *Staphylococcus aureus,*" *J. Clin Pathol.*, 34:559–563, 1981.

Yuk et al., "Minocycline as an alternative antistaphylococcal agent," *Rev. Infect. Dis.*, 13:1023–1024, 1991.

Zietkiewics et al., *Polski Tygodnik Lekarski*, 40(32):904–906, 1985.

Zinner et al., "Antistaphylococcal activity of rifampin with other antibiotics," *J. Infect. Dis.*, 144:365–374, 1981.

U.S. Pat. No. 4,107,121.
U.S. Pat. No. 4,442,133.
U.S. Pat. No. 4,678,660.
U.S. Pat. No. 4,749,585.
U.S. Pat. No. 4,895,566.
U.S. Pat. No. 4,917,686.
U.S. Pat. No. 4,952,419.
U.S. Pat. No. 5,013,306.
U.S. Pat. No. 5,217,493.

What is claimed is:

1. A composition comprising a non-glycopeptide antimicrobial agent other than vancomycin and a second agent selected from the group consisting of: (a) an anticoagulant, (b) an antithrombotic agent and (c) a chelating agent selected from the group consisting of: EGTA, diethylenetriamine penta acetic acid, DMSA, deferoxamine, dimercaprol, zinc citrate, a combination of bismuth and citrate, penicillamine, succimer and Etidronate, wherein the agents are included in a therapeutically effective amount between about 0.001 mg/ml and about 1000 mg/ml.

2. The composition of claim 1, comprising a non-glycopeptide antimicrobial agent and a chelating agent.

3. The composition of claim 2, wherein the chelating agent is EGTA.

4. The composition of claim 1, comprising a chelating agent selected from the group consisting of diethylenetriamine penta acetic acid, Etidronate and EGTA.

5. The composition of claim 1, comprising a non-glycopeptide antimicrobial agent and an anticoagulant.

6. The composition of claim 5, wherein the anticoagulant is heparin.

7. The composition of claim 5, wherein the anticoagulant is hirudin.

8. The composition of claim 1, wherein the non-glycopeptide antimicrobial agent selected from the group consisting of aminoglycoside, amphotericin B, ampicillin, carbenicillin, cefazolin, cephalosporin, chloramphenicol, clindamycin, erythromycin, gentamicin, griseofulvin, kanamycin, methicillin, nafcillin, novobiocin, penicillin, polymyxin, rifampin, streptomycin, sulfamethoxazole, sulfonamide, tetracycline, and trimethoprim.

9. The composition of claim 8, wherein the non-glycopeptide antimicrobial agent is a tetracycline antibiotic.

10. The composition of claim 9, wherein the tetracycline antibiotic is selected from the group consisting of chlortetracycline, oxytetracycline, demeclocycline, methacycline, minocycline and doxycycline.

11. The composition of claim 10, wherein the tetracycline antibiotic is selected from the group consisting of minocycline, doxycline and oxytetracycline.

12. The composition of claim 8, wherein the non-glycopeptide antimicrobial agent is selected from the group consisting of amphotericin B, chloramphenicol, gentamicin, griseofulvin, rifampin and sulfamethoxazole.

13. The composition of claim 1, further comprising a pharmacologically acceptable carrier solution.

14. The composition of claim 1, wherein the antimicrobial agent and the second agent is included in amounts ranging from about 1 to about 200 mg/ml.

15. The composition of claim 14, wherein the antimicrobial agent and the second agent is included in amounts ranging from about 2 to about 100 mg/ml.

16. The composition of claim 15, wherein the second agent is included in an amount from about 20 to about 60 mg/ml.

17. The composition of claim 16, wherein the antimicrobial agent is included in amounts ranging from about 2 to about 9 mg/ml.

18. The composition of claim 1, wherein the antimicrobial agent comprises a combination of a tetracycline antibiotic and a rifamycin antibiotic.

19. The composition of claim 1, wherein the antimicrobial agent is a tetracycline antibiotic and the second agent is a chelator.

20. The composition of claim 19, wherein the chelator is selected from the group consisting of diethylenetriamine pentaacetic acid, Etidronate and EGTA.

21. The composition of claim 20, wherein the chelator is EGTA.

22. The composition of claim 19, further comprising a therapeutically effective amount of a rifamycin antibiotic.

23. The composition of claim 1, wherein said chelating agent chelates Ca, Mg, Mn, Fe or Zn.

24. A medical device coated with a composition comprising a non-glycopeptide antimicrobial agent and a second agent selected from the group consisting of: (a) an anticoagulant, (b) an antithrombotic agent and (c) a chelating agent; wherein the agents are included in a therapeutically effective amount between about 0.001 mg/ml and about 1000 mg/ml.

25. The medical device of claim 24, wherein the composition comprises a chelating agent selected from the group consisting of EDTA, triethylene tetramine dihydrochloride, diethylenetriamine pentaacetic acid, Etidronate and EGTA.

26. The medical device of claim 24, wherein the composition comprises a non-glycopeptide antimicrobial agent and an anticoagulant.

27. The medical device of claim 26, wherein the anticoagulant is heparin.

28. The medical device of claim 26, wherein the anticoagulant is hirudin.

29. The medical device of claim 24, wherein the composition comprises a non-glycopeptide antimicrobial agent and a chelating agent.

30. The medical device of claim 29, wherein the chelating agent is EGTA.

31. The medical device of claim 30, wherein the non-glycopeptide antimicrobial agent is a tetracycline antibiotic.

32. The medical device of claim 31, wherein the tetracycline antibiotic is minocycline.

33. The medical device of claim 32, further defined as selected from the group of devices consisting of a central venous catheter, a peripheral intravenous catheter, an arterial catheter, a Swant-Ganz catheter, a hemodialysis catheter, an umbilical catheter, a percutaneous nontunneled silicone catheter, a cuffed tunneled central venous catheter and a subcutaneous central venous pert.

34. The medical device of claim 24, wherein the non-glycopeptide antimicrobial agent is selected from the group consisting of aminoglycoside, amphotericin B, ampicillin, carbenicillin, cefazolin, cephalosporin, chloramphenicol, clindamycin, erythromycin, gentamicin, griseofulvin, kanamycin, methicillin, nafcillin, novobiocin, penicillin, polymyxin, rifampin, streptomycin, sulfamethoxazole, sulfonamide, tetracycline, trimethoprim, and vancomycin.

35. The medical device of claim 34, wherein the non-glycopeptide antimicrobial agent is a tetracycline antibiotic.

36. The medical device of claim 35, wherein the tetracycline antibiotic is selected from the group consisting of chlortetracycline, oxytetracycline, demeclocycline, methacycline, minocycline and doxycycline.

37. The medical device of claim 36, wherein the tetracycline antibiotic is selected from the group consisting of minocycline, doxycycline and oxytetracycline.

38. The medical device of claim 34, wherein the non-glycopeptide antimicrobial agent is selected from the group consisting of amphotericin B, chloramphenicol, gentamicin, griseofulvin, rifampin and sulfamethoxazole.

39. The device of claim 34, coated with the combination of a tetracycline antibiotic and a chelator.

40. The device of claim 39, wherein the chelator is selected from the group consisting of EDTA, triethylene tetramine dihydrochloride, diethylenetriamine pentaacetic acid, Etidronate and EGTA.

41. The device of claim 39, wherein the composition further comprises a therapeutically effective amount of a rifamycin antibiotic.

42. The device of claim 41, coated with a combination of minocycline, rifampin and a chelator other than EDTA.

43. The medical device of claim 24, wherein the composition further comprises a pharmacologically acceptable carrier solution.

44. The medical device of claim 24, wherein the antimicrobial agent and the second agent is included in amounts ranging from about 1 to about 200 mg/ml.

45. The medical device of claim 44, wherein the antimicrobial agent and the second agent is included in amounts ranging from about 2 to about 100 mg/ml.

46. The medical device of claim 45, wherein the second agent is included in an amount from about 20 to about 60 mg/ml.

47. The medical device of claim 46, wherein the antimicrobial agent is included in amounts ranging from about 2 to about 9 mg/ml.

48. The medical device of claim 24, (wherein the antimicrobial agent comprises a combination of a tetracycline antibiotic and a rifamycin antibiotic.

49. A medical device prepared by a process comprising exposing the medical device to a composition comprising a non-glycopeptide antimicrobial agent and a second agent selected from the group consisting of a chelating agent, an anticoagulant, and an antithrombotic agent, wherein the agents are included in a therapeutically effective amount between about 0.001 mg/ml and about 1000 mg/ml.

50. The medical device of claim 49, wherein the process comprises treating the device with a surfactant before exposing the device to the composition.

51. The medical device of claim 50, wherein the surfactant is selected from the group of surfactant consisting of tridodecylmethyl ammonium chloride and benzalkonium chloride.

* * * * *

UNITED STATES PATENT AND TRADEMARK OFFICE
CERTIFICATE OF CORRECTION

PATENT NO. : 5,688,516

DATED : November 18, 1997

INVENTOR(S) : Isaam Raad et al.

It is certified that error appears in the above-identified patent and that said Letters Patent is hereby corrected as shown below:

On title page, item [75] add the following inventor:

--Rabih O. Darouiche, Houston, Tex.--.

Signed and Sealed this

Ninth Day of March, 1999

*Attest:*

Q. TODD DICKINSON

*Attesting Officer*      *Acting Commissioner of Patents and Trademarks*

(12) REEXAMINATION CERTIFICATE (4752nd)
United States Patent
Raad et al.

(10) Number: US 5,688,516 C1
(45) Certificate Issued: Mar. 18, 2003

(54) NON-GLYCOPEPTIDE ANTIMICROBIAL AGENTS IN COMBINATION WITH AN ANTICOAGULANT, AN ANTITHROMBOTIC OR A CHELATING AGENT, AND THEIR USES IN, FOR EXAMPLE, THE PREPARATION OF MEDICAL DEVICES

(75) Inventors: Isaam Raad, Houston, TX (US); Robert Sherertz, Winston-Salem, NC (US); Rabih O. Darouiche, Houston, TX (US)

(73) Assignees: Wake Forest University, Winston-Salem, NC (US); Board of Regents, The University of Texas, Austin, TX (US); Baylor College of Medicine, Houston, TX (US)

Reexamination Request:
No. 90/005,267, Feb. 19, 1999

Reexamination Certificate for:
Patent No.: 5,688,516
Issued: Nov. 18, 1997
Appl. No.: 08/317,309
Filed: Oct. 3, 1994

Certificate of Correction issued Mar. 9, 1999. 08/317,309

Related U.S. Application Data

(63) Continuation-in-part of application No. 08/150,472, filed on Nov. 12, 1993, now abandoned, which is a continuation-in-part of application No. 07/975,486, filed on Nov. 12, 1992, now Pat. No. 5,362,754.

(51) Int. Cl.⁷ .................... A01N 25/08; A01N 37/12; A61F 2/02; A61M 31/00
(52) U.S. Cl. .................. 424/409; 405/423; 514/566; 514/836; 604/53
(58) Field of Search ................. 424/405, 409, 424/423; 514/566, 836; 604/53

(56) References Cited

U.S. PATENT DOCUMENTS

| | | |
|---|---|---|
| 3,987,797 A | 10/1976 | Stephenson |
| 4,465,666 A | 8/1984 | Lukas et al. |
| 4,713,402 A | 12/1987 | Solomon |
| 4,919,889 A | 4/1990 | Jones et al. |
| 4,950,256 A | 8/1990 | Luther et al. |
| 4,980,163 A | 12/1990 | Blackburn et al. |
| 4,999,210 A | 3/1991 | Solomon et al. |
| 5,019,096 A | 5/1991 | Fox, Jr. et al. |
| 5,041,100 A | 8/1991 | Rowland et al. |

OTHER PUBLICATIONS

Russell, *Inhibition and Destruction of the Microbial Cell* (pp. 209–224) (1971).
*The Merck Index*, 11th Edition. Merck & Co., Inc. Publishers pp. 550, 606, 735, 738, 745 and 1035 (1989).
*Remington's Pharmaceutical Sciences*, 18th Edition. Alfonso R. Gennaro, Editor, Mack Publishing Company, Easton Pa. p. 1314 (1990).
Mandel, et al., Ed., *Principles and Practice of Infectious Diseases*, Third Edition. Churchhill Livingstone (p. 2189–96) (1990).
Wiernikowski, et al., *Bacterial Colonization of Tunneled Right Atrial Catheters in Pediatric Oncology: A Comparison of Sterile Saline and Bacteriostatic Saline Flush Solutions*, Am. J. Pediatr Hematol Oncol., vol. 13, No. 2 (pp. 137–140) (1990).
Schwartz, et al., *Prevention of Bacteremia Attributed to Luminal Colonization of Tunneled Central Venous Catheters with Vancomycin–Susceptible Organisms*, Journal of Clinical Oncology, vol. 8, No. 9 (p. 1591–97) (1990).

*Primary Examiner*—Carlos Azpuru

(57) ABSTRACT

Compositions and methods of employing compositions in flushing and coating medical devices are disclosed. The compositions include selected combinations of a chelating agent, anticoagulant, or antithrombotic agent, with an non-glycopeptide antimicrobial agent, such as the tetracycline antibiotics. Methods of using these compositions for coating a medical device and for inhibiting catheter infection are also disclosed. Particular combinations of the claimed combinations include minocycline or other non-glycopeptide antimicrobial agent together with EDTA, EGTA, DTPA, TTH, heparin and/or hirudin in a pharmaceutically acceptable diluent.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 6, 19 and 27 are cancelled.

Claims 1, 3, 5, 14–16, 20, 22, 24, 26, 44–46 and 49 are determined to be patentable as amended.

Claims 4, 7–13, 17–18, 21, 23, 25, 28–43, 47–48 and 50–51 dependent on an amended claim, are determined to be patentable.

1. A composition comprising a non-glycopeptide antimicrobial agent other than vancomycin, *a chelating agent selected from the group consisting of: EGTA, diethylenetriamine penta acetic acid, DMSA, deferoxamine, dimercaprol, zinc citrate, a combination of bismuth and citrate, penicillamine, succimer and Etidronate* and [a second] *an* agent selected from the group consisting of: (a) an anticoagulant, *other than heparin and* (b) an antithrombotic agent [and (c) a chelating agent selected from the group consisting of: EGTA, diethylenetriamine penta acetic acid, DMSA, deferoxamine, dimercaprol, zinc citrate, a combination of bismuth and citrate, penicillamine, succimer and Etidronate], wherein the agents are included in a therapeutically effective amount between about 0.001 mg/ml and about 1000 mg/ml.

3. The composition of claim [2] *1*, wherein the chelating agent is EGTA.

5. The composition of claim 1, comprising a non-glycopeptide antimicrobial agent *a chelating agent* and an anticoagulant.

14. The composition of claim 1, wherein the [antimicrobial agent and the second agent is] *agents are* included in amounts ranging from about 1 to about 200 mg/ml.

15. The composition of claim 14, wherein the [antimicrobial agent and the second agent is] *agents are* included in amounts ranging from about 2 to about 100 mg/ml.

16. The composition of claim 15, wherein the [second agent] *anticoagulant or antithrombotic agent* is included in an amount from about 20 to about 60 mg/ml.

20. The composition of claim [19] *9*, wherein the chelator is selected from the group consisting of diethylenetriamine pentaacetic acid, Etidronate and EGTA.

22. The composition of claim [19] *9*, further comprising a therapeutically effective amount of a rifamycin antibiotic.

24. A medical device coated with a composition comprising a non-glycopeptide antimicrobial agent, *a chelating agent* and [a second] *an* agent selected from the group consisting of: (a) an anticoagulant, *other than heparin and* (b) an antithrombotic agent [and (c) a chelating agent]; wherein the agents are included in a therapeutically effective amount between about 0.001 mg/ml and about 1000 mg/ml.

26. The medical device of claim 24, wherein the composition comprises a non-glycopeptide antimicrobial agent, *a chelator* and an anticoagulant.

44. The medical device of claim 24, wherein the [antimicrobial agent and the second agent is] *agents are* included in amounts ranging from about 1 to about 200 mg/ml.

45. The medical device of claim 44, wherein the [antimicrobial agent and the second agent is] *agents are* included in amounts ranging from about 2 to about 100 mg/ml.

46. The medical device of claim 45, wherein the [second] *anticoagulant or antithrombotic* agent is included in an amount from about 20 to about 60 mg/ml.

49. A medical device prepared by a process comprising exposing the medical device to a composition comprising a non-glycopeptide antimicrobial agent, *a chelating agent* and [a second] *an* agent selected from the group consisting of [a chelating agent], an anticoagulant, and an antithrombotic agent, wherein the agents are included in a therapeutically effective amount between about 0.001 mg/ml and about 1000 mg/ml.

* * * * *